United States Patent [19]

Gudibande et al.

[11] Patent Number: 5,597,910

[45] Date of Patent: Jan. 28, 1997

[54] ELECTROCHEMILUMINESCENT LABEL FOR DNA PROBE ASSAYS

[75] Inventors: Satyanarayana R. Gudibande, Rockville, Mass.; John H. Kenten, Gaithersburg, Md.

[73] Assignee: Igen, Inc., Gaithersburg, Md.

[21] Appl. No.: 479,817

[22] Filed: Jun. 7, 1995

Related U.S. Application Data

[63] Continuation of Ser. No. 307,026, Sep. 15, 1994, abandoned, which is a continuation of Ser. No. 805,537, Dec. 11, 1991, abandoned.

[51] Int. Cl.$^6$ .............................. C07H 21/04; C12Q 1/68; G01T 1/20; C09K 11/06
[52] U.S. Cl. .................... 536/24.3; 536/25.3; 536/25.32; 435/6; 435/91.1; 436/800; 436/801; 250/361 C; 252/301.16
[58] Field of Search ........................ 435/6, 91.1, 91.2; 536/24.3, 24.31, 24.32, 25.32, 26.41; 542/2, 26; 436/800, 801; 250/361 C; 252/301.16, 301.4

[56] References Cited

U.S. PATENT DOCUMENTS

| | | | |
|---|---|---|---|
| 4,725,677 | 2/1988 | Köster et al. | |
| 4,965,188 | 10/1990 | Mullis et al. | 435/6 |
| 5,061,445 | 10/1991 | Zoski et al. | |
| 5,135,717 | 8/1992 | Renzoni et al. | 422/61 |
| 5,247,243 | 9/1993 | Hall et al. | 324/71.1 |

FOREIGN PATENT DOCUMENTS

| | | |
|---|---|---|
| 33343/89 | 4/1989 | Australia . |
| 3334389 | 4/1989 | Australia . |
| 0178450 | 9/1985 | European Pat. Off. . |
| 0439036 | 1/1991 | European Pat. Off. . |
| WO86/02734 | 5/1986 | WIPO . |
| WO87/06706 | 11/1987 | WIPO . |
| WO89/04302 | 5/1989 | WIPO . |
| WO90/05411 | 5/1990 | WIPO . |
| WO90/05301 | 5/1990 | WIPO . |

OTHER PUBLICATIONS

Barone, A. D., Tang, J–Y, and Caruthers, M. H., "In situ activation of bis-dialkylaminophosphines –a new method for synthesizing deoxyoligonucleotides on polymer supports", Nucleic Acids Res., 12, 4051–61 (1984).

Beaucage, S. L., A Simple and Efficient Preparation of Deoxynucleoside Phosphoramidites In Situ, Pergamon Press Ltd., 375–378 (1984).

A. E. Friedman et al., "Luminescence of Ruthenium (II) Polypyridyls: Evidence for Intercalative Binding to Z–DNA", Nucleic Acids Research, vol. 19, No. 10, 1991 Oxford GB, pp. 2595–2602.

A. M. Pyle et al., "Mixed–Ligand Complexes of Ruthenium (II): Factors Governing Binding to DNA", Journal of the American Chemical Society, vol. 111, 1989 DC US, pp. 3051–3058.

H–Y Mei et al., "Chiral Probe for A–form Helices of DNA and RNA: Tris(tetramethylphenanthroline) ruthenium (II)", Journal of the American Chemical Society, vol. 108, No. 23, 12 Nov. 1986 DC US, pp. 7414–7416.

A. B. Tossi et al. "A Study of Some Polypyridylruthenium (II) Complexes as DNA Binders and Photocleavage Reagents", Photochemistry and Photobiology, vol. 49, No. 5, 1989 pp. 545–556.

G. F. Blackburn et al, "Electrochemluminescence Detection for Development of Immunoassays and DNA Probe Assays for Clinical Diagnostics", Clinical Chemistry, vol. 37, No. 9, issued 1991, pp. 1534–1539.

J. H. Kenten et al., "Rapid Electrochemiluminescence Assays of Polymerase Chain Reaction Products", Clinical Chemistry, vol. 37, No. 9, issued 1991, pp. 1626–1632.

M. Rodriguez et al., "Electrochemical Studies of the Interaction of Metal Chelates with DNA. 4. Voltammetric and Electrogenerated Chemiluminescent Studies of the Interaction of Tris (2, 2'–bipyridine)osmium (II) with DNA", Analytical Chemistry, vol. 62, issued 1990, pp. 2658–2662.

Willi Bannwarth et al., "A Simple Specific Labelling for Oligonucleotides by Bathophenanthroline–RuII Complexes as Nonradioactive Label Molecules", Tetrahedron Letters, vol. 30, No. 12, 1989, pp. 1513–1516.

Carole Yee et al., "Presence and Expression of Human Papillomavirus Sequences in Human Cervical Carcinoma Cell Lines", AJP, vol. 119, No. 3, Jun. 1985, pp. 361–366.

Y. Weinstein et al., "Cyclic GMP stimulates lymphocyte nucleic acid synthesis", Nature, vol. 251, Sep. 27, 1974, pp. 352–353.

Shibata et al., "Detection of Human Papilloma Virus in Paraffin–Embedded Tissue Using the Polymerase Chain Reaction", J. Exp. Med., vol. 167, Jan. 1988, pp. 225–230.

Patrick W. Gray et al., "Structure of the human immune interferon gene", Nature, vol. 298, Aug. 26, 1982, pp. 859–863.

Semih Erhan et al., "Do immunoglobulines have proteolytic activity?", Nature, vol. 251, Sep. 27, 1974, pp. 353–355.

Chin–Yih Ou et al., "DNA Amplification for Direct Detection of HIV–1 in DNA of Peripheral Blood Mononuclear Cells", Science, Jan. 15, 1988, pp. 295–297.

Biochemistry, Richard A. Cardullo et al., "Detection of nucleic acid hybridization by nonradiative fluorescence resonance energy transfer", Proc. Natl. Acad. Sci. USA, vol. 85, Dec. 1988, pp. 8790–8794.

Timothy V. Updyke et al., "Immunoaffinity Isolation of Membrane Antigens with Biotinylated Monoclonal Antibodies and Streptavidin–Agarose", Methods in Enzymology, vol. 121, 1986, pp. 717–725.

Kary B. Mullis et al., "Specific Synthesis of DNA in Vitro via a Polymerase–Catalyzed Chain Reaction", Methods in Enzymology, vol. 155, 1987, pp. 335–350.

Ralf Sommer et al., "Minimal homology requirements for PCR Primers", Nucleic Acids Research, vol. 17, No. 16, 1989, p. 6749.

Kenten et alii, "Rapid Electrochemiluminescence Assays of Polymerase Chain Reaction Products," Clinical Chemistry, vol. 37, No. 9, pp. 1626–1632, 1991.

Kenten et alii, "Improved Electrochemiluminescent Label for DNA Probe Assays: Rapid Quantitative Assays of HIV–1 Polymerase Chain Reaction Products," Clinical Chemistry, vol. 38, No. 6, pp. 873–879, 1992.

Bannwarth et alii, "A Simple Specific Labelling for Oligonucleotides by Bathophenanthroline–Ru" complexes as Nonradioactive label Molecules" *Tetrahedron Letters,* vol. 30, No. 12, pp. 1513–1516, 1989.

Blackburn et alii, "Electrochemiluminescence Detection for Development of Immunoassays and DNA Probe Assays for Clinical Diagnostics," *Clinical Chemistry,* vol. 37, No. 9, pp. 1534–1539, 1991.

Kenten, et al., *Clinical Chemistry,* 38/6, 873–879, 1992.

Kenten, et al., *Clinical Chemistry,* 37/9, 1626–1632, 1991.

Bannwarth, et al., *Tetrahedron Letters,* vol. 30, No. 12, pp. 1513–1516, 1989.

Blackburn, et al., *Clinical Chemistry,* 37/9, 1534–1539, 1991.

*Primary Examiner*—W. Gary Jones
*Assistant Examiner*—Bradley L. Sisson
*Attorney, Agent, or Firm*—Curtis, Morris & Safford

[57] ABSTRACT

This invention relates to a new electrochemiluminescent (ECL) label for oligonucleotides using phosphoramidite chemistry.

9 Claims, No Drawings

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CTCCACACTC TTTTGGATGC TCTGGTCATC      30

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CACATCATCC TCTGTTTGTG CTCTTTCCT      29

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CAGTTAATAC ACCTAATTAA CAAATCACAC         30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

ACAACATTAG AACAGCAATA CAACAAACCG         30

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CACCGCAGGC ACCTTATTAA TAAATTGTAT         30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GACACATTGG AAAAACTAAC TAACACTGGG         30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GAAAATGTGC TGACCGGACA TGAAAATGAG         30

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CTCATTTTCA TGTCCGGTCA GCACATTTTC         30

( 2 ) INFORMATION FOR SEQ ID NO:9:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (xi) SEQUENCE DESCRIPTION: SEQ ID NO:9:

TTTGTGACAC AGGTAGCACC GAATTAGCAC  30

(2) INFORMATION FOR SEQ ID NO:10:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (xi) SEQUENCE DESCRIPTION: SEQ ID NO:10:

ATAATCCACC TATCCCAGTG GAGAAAT  27

(2) INFORMATION FOR SEQ ID NO:11:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (xi) SEQUENCE DESCRIPTION: SEQ ID NO:11:

TTTGGTCCTT GTCTTATGTC CAGAATGC  28

(2) INFORMATION FOR SEQ ID NO:12:

(i) SEQUENCE CHARACTERISTICS:
    (A) LENGTH: 41 base pairs
    (B) TYPE: nucleic acid
    (C) STRANDEDNESS: single
    (D) TOPOLOGY: linear (xi) SEQUENCE DESCRIPTION: SEQ ID NO:12:

ATCCTGGGAT TAAATAAAAT AGTAAGAATG TATAGCCCTA C  41

ELECTROCHEMILUMINESCENT LABEL FOR DNA PROBE ASSAYS

This application is a continuation of application Ser. No. 08/307,026, filed Sep. 15, 1994, now abandoned, which is a continuation of Ser. No. 07/805,537, filed Dec. 12, 1991, now abandoned.

FIELD OF THE INVENTION

This invention relates to a new electrochemiluminescent (ECL) label for oligonucleotides using phosphoramidite chemistry. More specifically, this invention relates to the phosphoramidite of the tris (2,2-bipyridine) ruthenium (II) complex Bis (2,2-bipyridine) [4-{4-(2-cyanoethoxy-N,N-diisopropylamino)phosphinoxybutyl}4'-methyl]2,2-bipyridine ruthenium (II) dihexafluorophosphate which enables the direct incorporation of the label during automated DNA synthesis.

Several publications are referenced in this application by arabic numerals in parentheses. Full citation of these references is found at the end of the specification immediately preceding the claims. These references describe the state-of-the-art to which this invention pertains.

BACKGROUND OF THE INVENTION

Numerous methods and systems have been developed for the detection and quantitation of analytes of interest in biochemical and biological substances. Methods and systems which are capable of measuring trace amounts of microorganisms, pharmaceuticals, hormones, viruses, antibodies, nucleic acids and other proteins are of great value to researchers and clinicians.

A very substantial body of art has been developed based upon well known binding reactions, e.g., antigen-antibody reactions, nucleic acid hybridization techniques and protein-ligand systems. The high degree of specificity in many biochemical and biological binding systems has led to many assay methods and systems of value in research and diagnostics. Typically, the existence of an analyte of interest is indicated by the presence or absence of an observable "label" attached to one or more of the binding materials. Of particular interest are labels which can be made to luminesce through photochemical, chemical, and electrochemical means.

"Photoluminescence" is the process whereby a material is induced to luminesce when it absorbs electromagnetic radiation. Fluorescence and phosphorescence are types of photoluminescence. "Chemilumnescent" processes entail the creation of luminescent species by chemical transfer of energy. "Electrochemiluminescence" entails creation of luminescent species electrochemically.

Many chemiluminescent assay techniques, where a sample containing an analyte of interest is mixed with a reactant, labeled with a chemiluminescent label, have been developed. The reactive mixture is incubated and some portion of the labeled reactant binds to the analyte. After incubation, the bound and unbound fractions of the mixture are separated and the concentration of the label in either or both fractions can be determined by chemiluminescent techniques. The level of chemiluminescence determined in one or both fractions indicates the amount of analyte of interest in the biological sample.

Electrochemiluminescent (ECL) assaying techniques are an improvement over other assaying techniques. They provide a sensitive and precise measurement of the presence and concentration of an analyte of interest. In such techniques, the incubated sample is exposed to a voltametric working electrode in order to trigger luminescence. In the proper chemical environment, such electrochemiluminescence is triggered by a voltage impressed on the working electrode at a particular time and in a particular manner. The light produced by the label is measured and indicates the presence or quantity of the analyte. For a fuller description of such ECL techniques, reference is made to PCT published application Ser. No. 85/01253 (WO86/02734), PCT published application Ser. No. 87/00987 (WO87/06706) and PCT published application Ser. No. 88/03947 (WO89/04302). The disclosures of the aforesaid applications are incorporated by reference.

Additionally, U.S. patent application Ser. No. 267,509 and U.S. patent application Ser. No. 266,914 relate to preferred assay compositions; U.S. Pat. No. 5,061,445 and U.S. patent application Ser. No. 744,890, teach preferred apparatus for conducting ECL-base assays; and U.S. patent application Ser. No. 652,427 describes preferred methods and apparatus for conducting ECL-based assays. The disclosure of these patents and applications are incorporated by reference as well.

The methods taught in PCT published application Ser. No. 89/04919 (WO90/05301) permit the detection and quantitation of extremely small quantities of analytes in a variety of assays performed in research and clinical settings. However, the demands of researchers and clinicians always make it imperative to try to lower the detection limits of assays performed by these methods, to increase the sensitivities of those assays and to increase the speed at which they can be performed.

In particular, the demand exists for improved DNA probe assays. In this regard, applicants have found that analytes of interest can be detected using specific labeled compounds. Some of these labeled compounds are known, for example, from AU 33343/89 and from Bannwarth et al., "A Simple Specific Labelling for Oligonucleotides by Bathophenanthroline . $Ru^{II}$ Complexes as Nonradioactive Label Molecules", Tetrahedron Letters, Vol. 30, No. 12, pp. 1513–1516, 1989, and others are new.

OBJECTS OF THE INVENTION

Accordingly, it is a primary object of the invention to provide a method of detecting a nucleic acid analyte of interest present in a sample using a specific labeled compound.

It is another and related object of the invention to provide a method of conducting a polymerase chain reaction or other primer-directed reaction to detect a nucleic acid of interest in an amplification product of the reaction by incorporating in the reaction a specific labeled compound.

It is yet another and related object of the invention to provide a method of detecting a nucleic acid analyte of interest in the product of a polymerase chain reaction or other primer-directed reaction by labeling at least one nucleic acid in the reaction with a specific labeled compound.

These and other objects of the invention will be readily apparent from the following description and claims.

SUMMARY OF THE INVENTION

In one aspect, the objects of the invention are achieved using a compound of the formula:

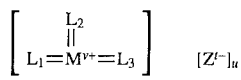

wherein M is selected from the group consisting of Ru, Os and Re; u.t=v, u is 1 or 2 and t is 1 or 2; $L_1$, $L_2$, and $L_3$ are the same or different and each is

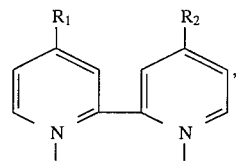

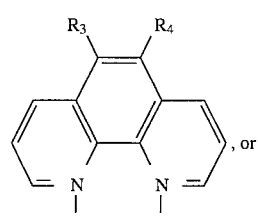

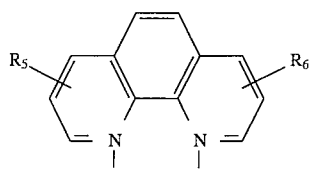

wherein $R_1$, $R_2$, $R_3$, $R_4$, $R_5$ and $R_6$ are the same or different and each is H, an alkyl group of 1–5 carbon atoms,

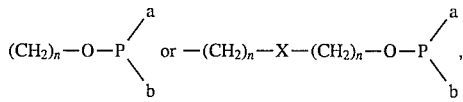

and at least one of $R_1$, $R_2$, $R_3$, $R_4$, $R_5$ and $R_6$ is either

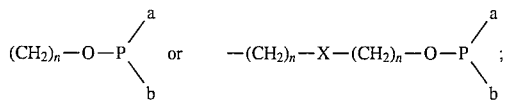

n is an integer in the range from 1–20; X is selected from the group consisting of O, S, $SO_2$, COO, and CONH; a and b are —N(CH—$(CH_3)_2)_2$, —NH—CH—$(CH_3)_2$, O—$(CH_2)_2$—CN, O—$CH_3$ or morpholino, provided that a and b are not the same; and Z is a counterion associated with M; it being further provided that ligands $L_1$, $L_2$ and $L_3$ are selected such that the compound is capable of electrochemiluminescence.

In a second aspect, the objects of the invention are achieved using a compound of the formula:

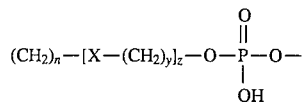

wherein M, $L_1$, $L_2$ and $L_3$ are as defined above provided, however, that one of the $R_1$–$R_6$ groups included in the definition of $L_1$, $L_2$ and $L_3$ is a linker of the formula

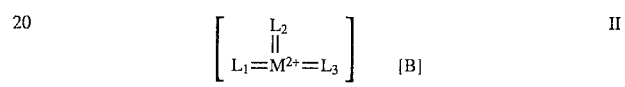

wherein n and X are as defined above; y is an integer of from 1–20; z is 0 or 1; and B is a biomolecule or a synthetic analog thereof, and the phosphodiester group is bound to said biomolecule; said compound being capable of electrochemiluminescence.

In another aspect, the objects of the invention are achieved using a specific compound of the formula:

III

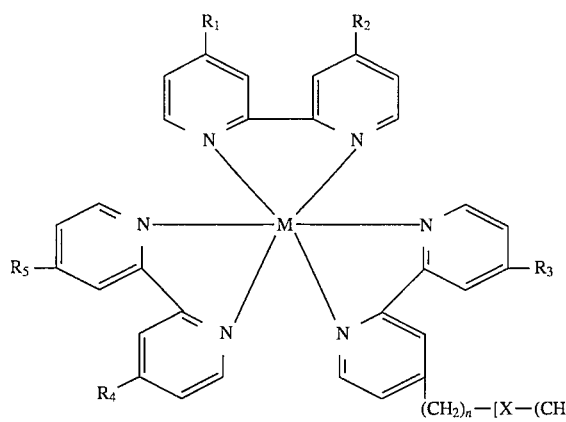
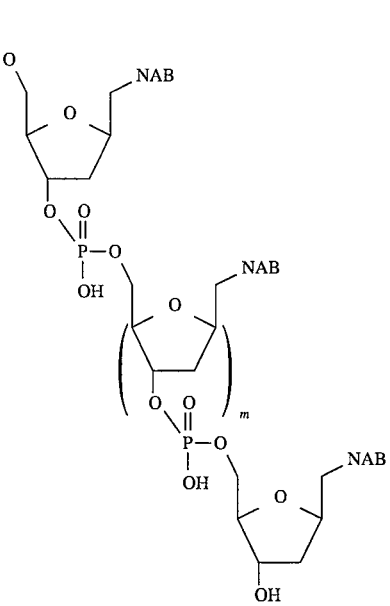

wherein M, $R_1$, $R_2$, $R_3$, $R_4$, $R_5$, n, X, y and z are as defined above; m is an integer of from 1–1000; and NAB is a nucleic acid base which may be modified or unmodified, said compound being able to electrochemiluminesce.

In yet another aspect, the objects of the invention are achieved for a method of detecting a nucleic acid analyte of interest present in a sample by contacting said sample with a probe of the formula III above, under conditions wherein said probe selectively binds to said analyte of interest to form an analyte of interest—probe complex, and measuring the electrochemiluminescence of said complex.

In still another aspect, the objects of the invention are achieved in a method of conducting a polymerase chain reaction or other primer-directed reaction so as to detect a nucleic acid of interest in an amplification product of said polymerase chain reaction or other primer-directed reaction by:

(a) incorporating in said polymerase chain reaction or other primer-directed reaction a primer of the formula III above;

(b) conducting a polymerase chain reaction or other primer-directed reaction; and (c) measuring the electrochemiluminescence of the amplified nucleic acid of interest.

In a further aspect, the objects of the invention are achieved for a method of detecting a nucleic acid of interest in the product of a polymerase chain reaction or other primer-directed reaction by:

(a) labeling at least one nucleic acid in said reaction with a compound of the formula III above;

(b) conducting a polymerase chain reaction or other primer-directed reaction which incorporates said nucleic acid into an amplification product; and (c) measuring the electrochemiluminescence of said nucleic acid of interest.

DESCRIPTION OF CERTAIN PREFERRED EMBODIMENTS

Definitions

In order to understand more clearly the invention, a general definition of certain terms is given below.

A "nucleotide" is one of four bases: adenine, cytosine, guanine, and thymine (DNA) or uracil (RNA), plus a sugar (deoxyribose for DNA, ribose for RNA), plus a phosphate. In order to provide monomers for a DNA polymerization reaction, typically all four of the deoxynucleotide triphosphates are required. A nucleotide as defined herein may also include modified bases such as 5-methyl-dCTP and 7-deaza-dGTP used to improve the action of polymerase on templates. The term nucleotide as used herein also includes bases linked to biotin and digoxigenin (Digoxigenin-11-UTP from Boehringer Mannheim, Indianapolis, Ind.), and biotin-21-UTP and amino-7-dUTP (Clontech, Palo Alto, Calif.) which may be incorporated directly into a primer or into a primer extension product during amplification, to provide for selective binding of amplified sequences.

An "oligonucleotide" is a sequence formed of at least two nucleotides.

A "polynucleotide" is a long oligonucleotide and may be either RNA or DNA.

While the term oligonucleotide is generally used in the art to denote smaller nucleic acid chains, and "polynucleotide" is generally used in the art to denote larger nucleic acid chains including DNA or RNA chromosomes or fragments thereof, the use of one or the other term herein is not a limitation or description of size unless expressly stated to be.

It is also well known to the art that the term "nucleic acid" refers to a polynucleotide of any length, including DNA or RNA chromosomes or fragments thereof with or without modified bases as described above.

A "sequence" (e.g. sequence, genetic sequence, polynucleotide sequence, nucleic acid sequence) refers to the actual enumerated bases (ribose or deoxyribose) present in a polynucleotide strand reading from the 5' to 3' direction.

A "specific or selected" nucleotide sequence refers to a particular sequence distinguishable (i.e., by hybridization analysis) from other different sequences (e.g., the specific nucleotide sequence 5'-ATGCCC-3' is not the same sequence as 5'-AAGCCC-3').

A "probe" is a single or double stranded nucleic acid which has a sequence complementary to a target nucleic acid sequence of interest and which has some additional feature enabling the detection of the probe—target duplex. The artisan will understand that if the probe and/or the target is double stranded, the double stranded nucleic acid must undergo strand separation before hybridization can take place.

A probe is rendered detectable by an attached tag or marker. A tag or marker linked to a probe may include a fluorescent or luminescent tag, an isotopic (e.g. radioisotope or magnetic resonance) label, a dye marker, an enzyme marker, an antigenic determinant detectable by an antibody, or a binding moiety such as biotin enabling yet another indicator moiety such as a streptavidin coated bead to specifically attach to the probe. When the labeled or tagged probe—target duplex is formed, that duplex may be detected by the characteristic properties of the tag or label. Alternatively, as described for the ECL assays in the following examples, the probe with its binding moiety allows the capture of labeled target, via hybridization and duplex formation, allowing detection by a label or other art known means.

The term "label" or "labeled" when applied to a nucleic acid means that the nucleic acid in question is linked to a moiety which is detectable by its properties which may include: luminescence, electrocemiluminescence, catalysis of an identifying chemical substrate, radioactivity, or specific binding properties. Thus, the term "label" includes ligand moieties unless specifically stated otherwise.

A "primer" is a relatively short segment of oligonucleotide which is complementary to a portion of the sequence of interest (the sequence of interest can be a subfragment within a larger nucleic acid sequence). A primer represents a 5' terminus of the resulting extension product. A primer which is complementary at its 3' terminus to the sequence of interest on the template strand enables this 3' terminus to be acted on by a polymerase on hybridization to the template. It is well known that modifications to the 3' end will affect the ability of an oligonucleotide to function as primer. An example is the incorporation of a dideoxynucleotide as in DNA sequencing thus preventing the action of DNA polymerases. It is well known that the length of the primer will depend upon the particular application, but that 20–30 base pairs is a common size. As is well known, a primer need not be a perfect complement for successful hybridization to take place. If the primer is an imperfect complement, an extension product will result which incorporates the primer sequence, and during a later cycle, the complement to the primer sequence will be incorporated into the template sequence. Thus, it is well known that a properly selected primer having a sequence altered from that of the complement of the template may be used to provide in vitro mutagenesis. The primer may incorporate any art known nucleic acid bases, including any art known modified or labeled bases as defined above so that the primer extension product will incorporate these features to permit separation and detection of the primer extension product. A tag or marker advantageously linked to a primer may include a fluorescent or luminescent tag, an ECL label, an isotopic (e.g. radioisotope or magnetic resonance) label, a dye marker, an enzyme marker, an antigenic determinant detectable by an antibody, or a binding moiety such as biotin enabling yet another indicator moiety such as a streptavidin coated bead to specifically attach to the primer or any nucleic acid sequence incorporating that primer. When the labeled or tagged amplification product is formed, that amplification product may be detected by the characteristic properties of the tag or label.

The specific or selected primer is distinguished from a "universal primer" which will indiscriminately anneal to any DNA sequence to which a complementary (to the primer) adaptor terminal sequence has been attached. With a universal primer care must be taken to isolate the nucleic acid of interest, or otherwise direct the ligation procedure only to the desired DNA sequence of interest, to avoid randomly attaching the adaptor to all nucleic acid sequences present.

The term "single primer" means a single, unpaired, specific or selected primer designed to selectively hybridize with a target nucleic acid sequence of interest.

"Single primer amplification" is a method for amplifying a nucleic acid utilizing only a single, unpaired primer which is complementary to a portion of the sequence of interest.

"Hybridization" describes the formation of double stranded or duplex nucleic acid from complementary single stranded nucleic acids. Hybridization may take place between sufficiently complementary single stranded DNA and/or RNA to form: DNA-DNA, DNA-RNA, or RNA-RNA.

"Annealing" refers to hybridization between complementary single chain nucleic acids when the temperature of a solution comprising the single chain nucleic acids is lowered below the melting or denaturing temperature.

The in vitro amplification of DNA is catalyzed by DNA polymerase. A number of types of DNA polymerase are known to the art. They generally share the common property of catalyzing the synthesis of a double stranded DNA sequence utilizing a single stranded template to which a primer is annealed. DNA polymerases extracted from most organisms become inactive at the temperatures required for thermal denaturing of nucleic acids. Thus, replacement of the enzyme at the start of each thermal cycle, or the addition Of a factor able to prevent heat inactivation, is required if such heat sensitive enzymes are utilized. The DNA polymerases which are preferred for in vitro PCR are derived from organisms which thrive at high temperatures and thus are heat resistant (do not lose catalytic activity at the temperature which denatures duplex DNA).

The reaction catalyzed by DNA polymerase is known to the art, and referred to herein as the "DNA polymerase reaction". The reaction as modified herein requires a buffer solution as known to the art, a supply of DNA template (the DNA sequence of interest), some or all (depending on template sequence composition) of the four deoxyribonucleotide triphospates (which may include modified bases as described above), a single specific primer designed to hybridize to or near the 3' terminal of the template, preferably used in a molar excess of 1000:1 with respect to the nucleic acid of interest, and a means for cyclic strand separation. Strand separation is preferably achieved by thermal cycling between annealing and denaturation temperatures. Reverse transcriptase is known to mediate both RNA to DNA copying, as well as DNA to DNA copying. Hence, any number of enzymes now known will catalyze the chain reaction.

"Electrochemiluminescent (ECL) labels" are those which become luminescent species when acted on electrochemically. They provide a sensitive and precise measurement of the presence and concentration of an analyte of interest. In such techniques, the sample is exposed to a voltammetric working electrode in order to trigger luminescence. The light produced by the label is measured and indicates the presence or quantity of the analyte. Such ECL techniques are described in PCT published applications by Bard et al. (PCT U.S. patent application Ser. No. 85/02153, WO86/02734) and Massey et al. (PCT U.S. patent application Ser. No. 87/00987, WO87/06706).

An "ECL assay buffer" is a general diluent which contains tripropylamine that is necessary for the electrochemical reaction on the electrode in an ECL analyzer.

An "ECL diluent" is a diluent reagent used in diluting solutions containing labile biomolecules for storage purposes.

The terms "detection" and "quantitation" are referred to as "measurement", it being understood that quantitation may require preparation of reference compositions and calibrations.

"ECL apparatus" is any apparatus for performing electrochemiluminescence based assays.

Tag NHS (N-hydroxy-succinimide) and tag phosphoramidite are examples of ECL tags. The tag-NHS ester is useful for labeling substances containing free amino groups capable of reaction with the NHS ester to form an amide bond. (See, for example, WO86/02734). The tag phosphoramidite is useful for labeling substances containing free amino, sulphydryl, or hydroxyl groups forming phospholinkages, especially phosphodiester linkages.

DETAILED DESCRIPTION

The demand continues to exist for improved DNA probe assays. It has been found that highly sensitive nucleic acid probe assays can be carried out using specific labeled compounds.

In particular, highly sensitive nucleic acid probe assays can be carried out using a compound of the formula:

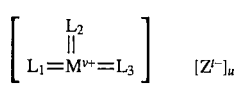

wherein M is selected from the group consisting of Ru, Os and Re; u.t=v, u is 1 or 2 and t is 1 or 2; $L_1$, $L_2$, and $L_3$ are the same or different and each is

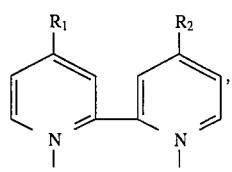

-continued

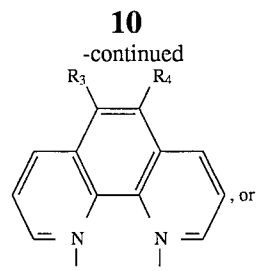

wherein $R_1$, $R_2$, $R_3$, $R_4$, $R_5$ and $R_6$ are the same or different and each is H, an alkyl group of 1–5 carbon atoms,

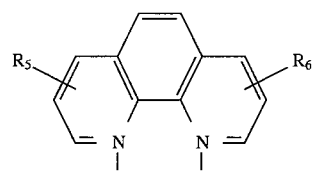

and at least one of $R_1$, $R_2$, $R_3$, $R_4$, $R_5$ and $R_6$ is either

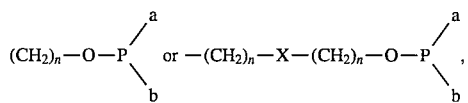

n is an integer in the range from 1–20; X is selected from the group consisting of O, S, SO$_2$, COO, and CONH; a and b are —N(CH—(CH$_3$)$_2$)$_2$, —NH—CH—(CH$_3$)$_2$, O—(CH$_2$)$_2$—CN, O—CH$_3$ or morpholino, provided that a and b are not the same; and Z is a counterion associated with M; it being further provided that ligands $L_1$, $L_2$ and $L_3$ are selected such that the compound is capable of electrochemiluminescence.

One embodiment uses a compound of formula I described above wherein $L_1$, $L_2$ and $L_3$ are all substituted or unsubstituted bipyridyl, and n is from 4 to 7, in a highly sensitive nucleic acid probe assay.

A particularly preferred embodiment uses the phosphoramidite of the tris (2,2-bipyridine) ruthenium (II) complex Bis (2,2-bipyridine) [4-{4-(2-cyanoethoxy-N,N-diisopropylamino)phosphinoxybutyl}4'-methyl]2,2bipyridine ruthenium (II) dihexafluorophosphate which enables the direct incorporation of the label during automated DNA synthesis. Similar results are obtained with complexes of osmium and rhenium.

Of course, the assays of the invention can similarly be used to detect nearly any biomolecule or synthetic analog thereof. However, the assays are particularly useful for detecting a nucleic acid analyte of interest, especially a nucleic acid sequence, present in a sample. The analyte of interest may be selectively bound to a probe or be a product of a polymerase chain reaction or other primer-directed reaction.

Similar compounds are taught, for example, in AU 33343/89. However, these compounds have an undesirable, nonspecific interaction with nucleic acids such as DNA. Moreover, the preferred compounds in the reference are the bathophenanthroline . Ru$''$ and benzbathophenanthroline . Ru$''$ complexes. The disadvantages of these compounds include their size and their lack of water solubility. Additionally, the aryl substituents on the complexes further the problem of size and they could interfere with an electrode during an ECL analysis. This reference appears to relate only to fluorescence. Fluorescence is the immediate emission (in the order of $10^{-8}$ sec) of light from a molecule after it has absorbed radiation. Time resolved fluorescence is based on the time taken for differing fluorophores to emit their fluorescence. Thus fluorophores with longer life times (0.1 to $10 \times 10^{-6}$ sec) are readily separated from those which are common (as contaminants in samples and containers) with short life times (10 to $1 \times 10^{-9}$ sec).

In contrast to fluorescence where the luminescence is produced by the absorption of radiant energy, the luminescence generated by ECL is produced by electrochemistry at the interface of an electrode. For example, with certain compounds of the invention, $Ru^{2+}$ is oxidized to $Ru^{3+}$, and then reacts with the electrochemical oxidation products of tripropyl amine to generate the excited state of $Ru^{2+}$ which emits its energy as light. This type of oxidative-reduction mechanism of excitation is in marked contrast to the excitation which occurs in the case of fluorescence. This difference is shown, for example, in the following chart which compares the fluorescence and ECL capabilities of a compound of the invention and of compounds taught in AU 3343/89. In particular, the chart compares the fluorescence and ECL capabilities between bipyridyl and bathophenanthroline Ru complexes.

| Cmpd | MW | Emission[1] | Rel. Floro. Int.[2] | Rel. ECL Int.[3] |
|---|---|---|---|---|
| Ru(Bpy)$_3$ *6(H$_2$O) | 748 | 615 nm | 1.0 | 1.0 |
| Ru(A)$_2$B | 1690 | 630 | 9.2 | 0.003 |
| Ru(A)$_2$C | 1850 | 630 | 7.3 | 0.096 |
| Ru(A)$_2$D | 1878 | 630 | 7.3 | 0.080 |

[1]excitation at 450 nm
[2]corrected for buffer emission
[3]corrected for buffer ECL A = 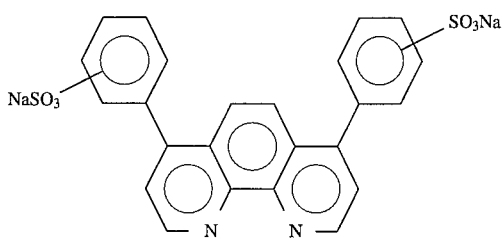

B = 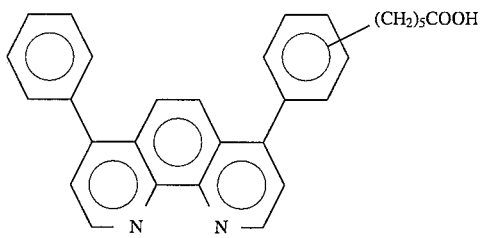

C = 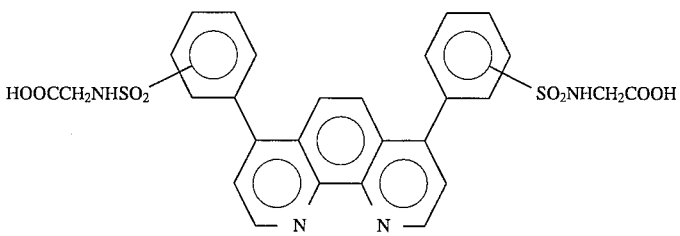

D = 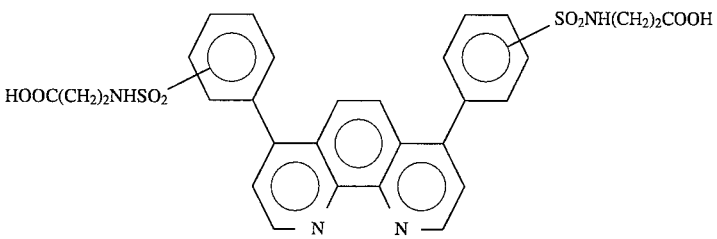

| Cmpd | MW | Emission[1] | Rel. Floro. Int.[2] | Rel. ECL Int.[3] |
|---|---|---|---|---|

BPY = 

The relative ECL capability of the compounds is substantially displayed by the compound when bound to a biomolecule or analog thereof.

The compounds of particular interest in the present invention are those in which the ratio of relative ECL capability of the compound to the relative ECL capability of the bipyridyl analog is greater than or equal to 0.10. Desirably, the ratio is at least 0.25, and preferably is 1.0 or higher.

In order to better understand the invention, a number of examples follow which are not intended in any way to limit the scope of the invention. They are simply provided to illustrate the invention to the skilled artisan.

EXAMPLE I

Synthesis of Label (Tag-Phosphoramidite)

1(a). Synthesis of THP-Derivative of Bromo Alkanol

This synthetic scheme may be better understood by referring to Scheme 1a) below.

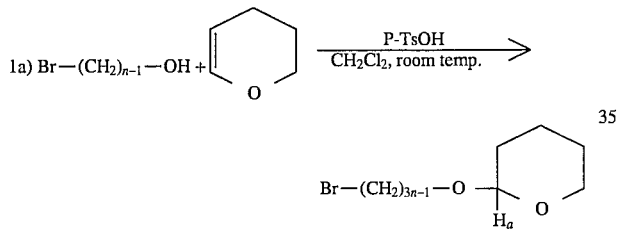

The following procedure is for the synthesis of bipyridine ligand with 4-carbon spacer arm. However, the same synthesis procedure has been used without any modification for the synthesis of a 7-carbon bipyridine ligand using THP-derivative of bromohexanol.

3-bromo-1-propanol, 12.5 g (~90 m.mole.), was placed in a 250 ml round bottom flask. Dichloromethane, 50.0 ml, and 100 mg P-toluenesulfonic acid were added to the flask. The solution was stirred on a magnetic stir plate. 3,4-dihydro-2H-pyran, 9.2 g (~110 m.mole.), was dissolved in 80 ml of dichloromethane and the resulting solution was placed in a pressure equalized addition funnel. The 3,4-dihydro-2H-pyran solution in the addition funnel was added to he solution in the flask over a period of 1 h. The solution in the flask turned either a light or dark green in color. The progress of the reaction was checked by TLC on silica-gel plate in 50% hexane: 50% ethylacetate. The TLC plate was developed by dipping the plate in a solution of phosphomolybdic acid and warming it on a hot plate. The product, a THP-derivative of 3-bromo-1-propanol has an $R_f$~1.0, and the unreacted 3,4-dihydro-2Hpyran has an $R_f$~0.5 (exhibits streaking). The TLC demonstrated that the reaction went to completion in about 1 hour after the addition of the 3,4-dihydro-2H-pyran as indicated by a major single spot with an $R_f$~1.0. The reaction was then quenched by the addition of 100 ml of 20% sodium bicarbonate solution followed by extraction of the aqueous layer twice with 100 ml of dichloromethane. The combined dichloromethane layer was dried over 50 g anhydrous sodium sulfate and rotary evaporated to obtain an oily product.

The final (oily) product was purified by silica gel column chromatography using 5% ethyl acetate: 95% hexane as the mobile phase. The chromatography was monitored by TLC using the solvent conditions described above. Fractions containing pure product were pooled and the solvent was removed by rotary evaporation, resulting in 16.0 g of pure, clear oily product. The yield of this reaction step was about 75±5%.

The nmr $^1$H-nmr spectrum shows a multiplet at 4.55 ppm which is characteristic of the $H_a$ proton of the THP-group (as shown in reaction scheme I).

$^1$H-nmr spectral data of THP-derivative of 3-bromo prapanol: $^1$H-nmr (CDCl$_3$), δ1.30–1.80(m,6); 2.06(qn., 2); 3.40–3.50(m,4); 3.74–3.83(m,2) and 4.50–4.57(m,1).

1 (b). Alkylation Reaction

This synthetic scheme may be better understood by referring to Scheme 1b) below.

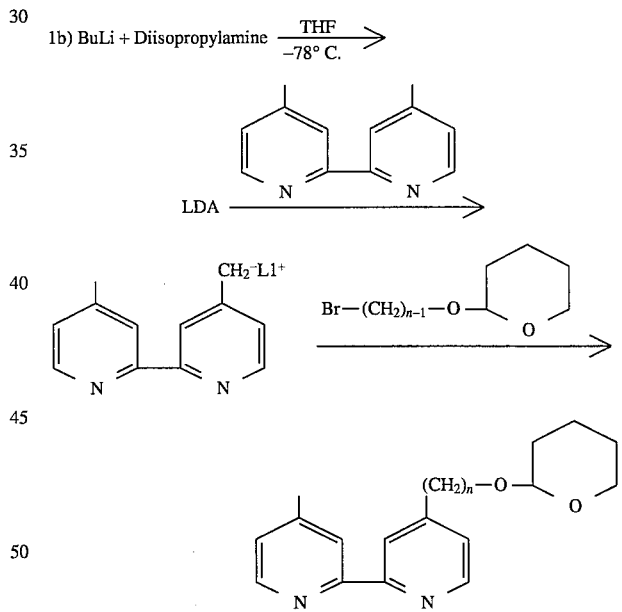

The procedure utilized the in situ generation of lithium diisopropylamide (LDA). A 500 ml round bottom flask was dried in an oven and cooled in a desiccator in order to remove moisture prior to use. Diisopropylamine, 3.1 ml (~22 m.mole.), was placed in the 500 ml round bottom flask together with 15.0 ml of dry tetrahydrofuran (THF). The mouth of the flask was equipped with a three-way stopcock. One of the outlets of the stopcock was connected to an argon-filled balloon and the other outlet was sealed with a rubber septum in order to facilitate introduction of reagents using a syringe. The flask was cooled at −78° C. in a constantly stirred dry ice—isopropyl alcohol cooling bath to which both dry ice and isopropyl alcohol were added as needed to maintain the bath temperature. After half an hour 14.0 ml (~22 m.mole.) of butyllithium was slowly added to the diisopropylamine solution. After the addition, the reaction flask was carefully raised from the cooling bath for 10 min., and then re-immersed into the cooling bath.

4,4'-dimethyl-2,2'-bipyridine, 3.68 g (~20.0 m.mole.), was ground into a fine powder in a pestle and mortar. This was dissolved in 80.0 ml of dry tetrahydrofuran (THF) in a 250 ml round bottom flask. The reaction flask was raised just above the surface of the cooling bath, and the bipyridine solution was slowly added. Upon addition of the bipyridine solution the reaction mixture turned dark purple in color. After the complete addition of the bipyridine solution the flask was re-immersed in the cooling bath and the reaction mixture was stirred in the cooling bath for two hours. A THP-derivative of 3-bromo-1-propanol, 6.0 g (~26.0 m.mole.), was placed in a 100 ml round bottom flask and then about 10–15 ml dry THF was added and the solvent was evaporated on a rotary evaporator. The process of addition and evaporation of dry THF was repeated two more times, and each time the vacuum was released to argon. Finally, the residue was dissolved in 5.0 ml of dry THF and the resulting solution was added to the reaction mixture and stirred for another hour. The reaction was checked by TLC on silica-gel plate with 10% methanol: 90% chloroform as the mobile phase. The TLC revealed two spots. The slower moving (unreacted) 4,4'-dimethyl-2,2'-bipyridine has an $R_f$~0.35, and the faster moving alkylated product has an $R_f$~0.42. A successful reaction was indicated when the TLC spot corresponding to the desired product represented more than 60% by mass with respect to untreated starting material. The reaction mixture was then allowed to stir overnight. No further addition of either the dry ice or the isopropyl alcohol to the cooling bath was necessary.

The TLC of the reaction was checked again the next day. The reaction was then quenched by adding 100 ml of saturated $NH_4Cl$ solution and the quenched mixture was transferred to a separatory funnel. After shaking, followed by settling of the mixture, the solution separated into a bottom aqueous layer and a top THF layer. The THF layer was then separated and dried over anhydrous sodium sulfate. The aqueous layer was extracted twice with 150 ml of dichloromethane. The combined organic layer was dried over anhydrous sodium sulfate and rotary evaporated to obtain an oily residue. The reaction mixture was purified after the deprotection of THP group as described below in 1(c).

1(c). Deprotection of THP-Group and Purification by Column Chromatography

This synthetic scheme may be better understood by referring to Scheme 1c) below.

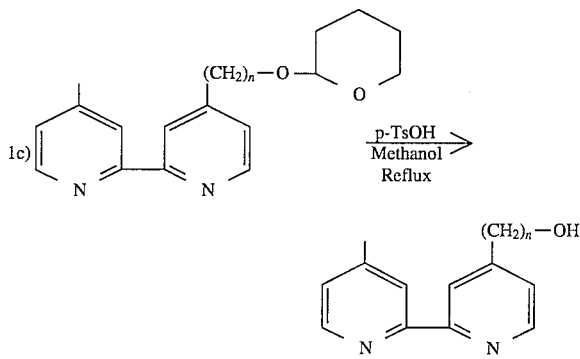

The $R_f$ difference between the unreacted 4,4'-dimethyl-2,2'-bipyridine and the alkylated product is very small. Hence, it is preferable to carry-out the purification of the bipyridine ligand after the deprotection of the THP-group which results in a considerable $R_f$ difference between the desired product and the impurity.

| COMPOUND | $R_f$ |
|---|---|
| THP-derivative of 4-carbon bipyridine ligand | 0.42. |
| 4,4'-dimethyl-2,2'-bipyridine (unreacted) | 0.35. |
| 4-carbon bipyridine ligand (alcohol ligand) | 0.15. |

40 ml of methanol was added to the oily residue from the alkylation reaction (section 1(b)) and placed in a 250 ml round bottom flask. The oily residue contains a mixture of unreacted 4,4'-dimethyl-2,2'-bipyridine, THP-derivative of bipyridine ligand (the desired product), and the unreacted THP-derivative of 3-bromo-1-propanol. P-toluenesulfonic acid, 5.0 g (~25 m.mole.), was added to the reaction mixture followed by stirring at room temperature for 1 h. The reaction was monitored by TLC on silica gel plates with 10% methanol: chloroform as the mobile phase. The $R_f$ values for various components were: unreacted 4,4'-dimethyl-2,2'-bipyridine $R_f$~0.35, THP-derivative of bipyridime ligand with spacer arm $R_f$~0.42, and the bipyridine alcohol ligand with the spacer arm $R_f$~0.15. Completion of the reaction was indicated by the disappearance of the spot corresponding to the THP-derivative of bipyridine ligand ($R_f$~0.42) on TLC. The solvent (methanol) was then evaporated on a rotary evaporator, and the residue resuspended in 10 ml of dichloromethane, to which 40.0 ml of saturated solution of sodium bicarbonate was added. The aqueous layer was then extracted twice with 100 ml of dichloromethane. The combined organic layer was dried over anhydrous sodium sulfate, and the solvent was stripped-off on rotary evaporator, yielding an oily residue as the product.

The oily product was purified by silica gel column chromatography using 2% methanol: 98% chloroform as mobile phase. The column was monitored by TLC on silica gel with 10% methanol: 90% chloroform. The pure fractions (as judged by TLC) were pooled and the solvent was removed by rotary evaporation. The yield of the alkylation reaction was very much dependent on the maintenance of dry conditions during the reaction as well as on the freshness of reagents such as butyllithium. The yield of this alkylation reaction step was about 60±10%. The compound was characterized by recording a $^1H$-NMR spectrum of the sample.

$^1H$-NMR spectral data of bipyridine alcohol ligand: $^1H$-NMR ($CDCl_3$), $\delta$1.54–1.64(m,2); 1.68–1.80(m,2); 2.45(s,AR—$CH_3$); 2.66–2.75(t,2); 3.59–3.68(t,2); 7.09–7.20(m,2 Ar—H); 8.20 (S,2 Ar—H) 8.50–8.60 (m, 2 Ar—H).

2. Preparation of Tris-Bipyridine Ruthenium (II) Complex Tag-Alcohol)

This synthetic scheme may be better understood by referring to Scheme 2) below.

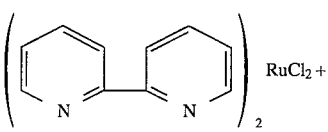

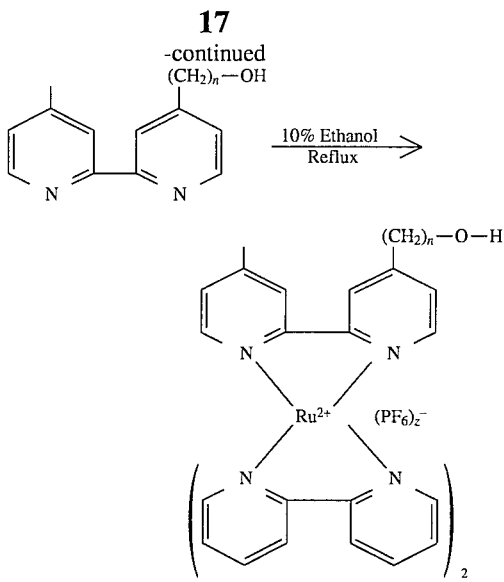

Cis-dichloro-bis(bipyridine) ruthenium (II) dihydrate, 1.040 g (2.0 m.mole.), and 530.0 mg (~2.2 m.mole.) of 4-carbon bipyridine ligand (from section 1C), were placed in a 250 ml round bottom flask, 50.0 ml of 10% ethanol in water was added, and the solution was purged with argon gas for 10–15 min. The flask was fitted with a water cooled condenser, and the mixture was refluxed for 6 h to form the tris-bipyridine ruthenium (II) complex. The flask was covered with aluminum foil during refluxing. The solvent was removed by rotary evaporation, and then the complex was dissolved in a minimum amount of deionized water and loaded onto the ion-exchange column.

The usual purification procedure used 7.0 g of the ion-exchange resin to purify 1.3 g (~2.0m.mole.) of the complex by column chromatography. The resin was allowed to swell in 300 ml of deionized water for 2–3 h, and then the swelled resin was packed into a column 30 cm in length and 2.5 cm in inner diameter to a height of 15 cm. The resin was then layered with washed and dried sand to a height of 0.5 cm and the column washed with 250 ml of deionized water. The Tag-alcohol from the complex formation reaction from section 2 was dissolved in a minimum amount of deionized water and was carefully layered onto the top of the resin. The chromatogram was developed by washing the column with 250 ml of deionized water. During this wash step, a light yellow colored impurity began separating from the main band (deep-red in color). This impurity was driven-off the column by washing the column with ~350 ml of 10 mM NaCl solution. The eluant was later switched to 100 mM NaCl solution. After this, the main deep-red colored band began eluting, and most of the desired product was eluted in a volume of 500–600 ml. A dark brown colored material was adsorbed onto the column permanently and was not eluted from the column even under very high ionic strength buffer (2–3M HCl and NaCl).

The eluted Tag-alcohol was then precipitated using ammonium hexafluoro-phosphate by the following procedure. The eluate was heated to boiling with constant stirring, and then allowed to cool to 75°–80° C., followed by the addition of ammonium hexafluorophosphate in small amounts, using a spatula, until a stable precipitate appeared (precipitate appeared and did not go into solution again). The solution was first brought to room temperature (20°–25° C.) and then cooled to 4° C. overnight. The resulting precipitate was collected on a Buchner funnel fitted with a fitted disc (10–15 µ), and then dried under vacuum. The average yield of this complexation reaction after column purification was found to be >80%. The molecular weight of the complex at this stage is ~945.45 (excluding water of hydration).

The Tag-alcohol prepared and purified by the above procedure was then analyzed by HPLC and $^1$H-nmr spectroscopy. HPLC characterization was performed on Perkin-Elmer HPLC instrument with a Beckman $C_{18}$-reverse phase column. The mobile phase consisted of buffers: A) 50 0.10M triethylammonium acetate, pH 7.25: 50% acetonitriile, and B) 90% acetonitrile: 10% 0.10M triethylammonium acetate, pH 7.25. The chromatography was run under isocratic condition with 80% buffer B. The flow rate was maintained at 1.0 ml/min., and elution was monitored by absorbance at 280 nm.

Tag-alcohol, 2.0 mg, was dissolved in 100 µl of buffer B. Then 1.0 µl of this stock solution was diluted to 400 µl with buffer B. 50 µl of this diluted solution was injected into the HPLC instrument. The Tag-alcohol eluted as a single major peak between 22–23 min. The purity of the Tag-alcohol, as determined by integration of the elution peak, was 95±3%.

The $^1$H-nmr spectrum was recorded on a GE-300 MHz FT-nmr instrument. In a typical analysis, 30 mg of Tag-alcohol was dissolved in 500 µl of $CD_3CN$. The $^1$H-NMR also clearly indicated that the purity of the material was satisfactory.

$^1$H-NMR spectral data of Tag-alcohol: $^1$H-NMR ($CD_3CN$) δ1.52–1.65(m,2); 1.72–1,85(m,2); 2.20(s,3 Ar—$CH_3$); 2.82–2.90(m,2); 3.50–3.60(m,2); 7.23–7.32(m, 2, 5'Ar—H); 7,38–7.48 (m, 4, 4 Ar—H); 7.42–7.52 (m, 2 3 ' Ar—H); 7.52–760(m,4, 3 Ar—H); 8.02–8.14(m,4, 5 Ar—H); 8.38–8.44(d,2, 6' At-H) and 8.50–8.56(d,4, 6 Ar—H).

3. Phosphitylation Reaction

This synthetic scheme may be better understood by referring to Scheme 3) below.

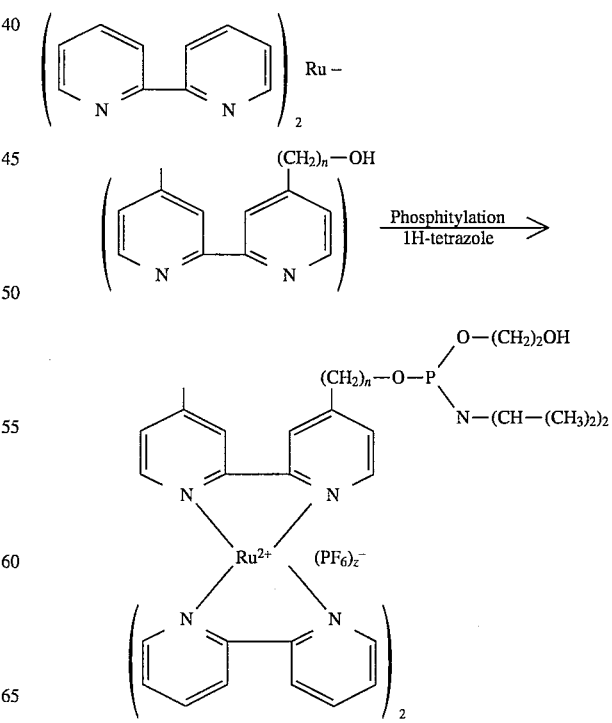

Tag-alcohol, 945 mg (~1 m.mole.), and 35.0 mg (~0.5 m.mole.) of ¹H-tetrazole were placed in a 50 ml round bottom flask. 10 ml of freshly distilled dry acetonitrile (distilled over $CaH_2$) was added and rotary evaporated. The addition and evaporation of dry acetonitrile was performed three times to ensure that the material was devoid of moisture. Finally, the mixture of Tag-alcohol and tetrazole was redissolved in 3.0 ml of dry acetonitrile. During the course of the entire sequence of operations the reaction flask was maintained under argon atmosphere. 2-cyanoethyl-N,N,N',N'-tetra-isopropylphosphorodiamidite (phosphitylating agent), 500 μl (~1.6 m.mole.), was added to the stirring reaction mixture. The reaction was allowed to proceed for 1 h., covered by aluminum foil. The reaction was stopped by addition of 10.0 ml of a saturated sodium chloride solution and the aqueous layer was extracted thrice with 25 ml of dichloromethane. The combined organic layer was dried over anhydrous sodium sulfate and the solvent was removed by rotary evaporation. The foamy residue was dried extensively under vacuum. The material was dissolved in 15–20 ml of dry dichloromethane and the solution was slowly added to a stirring solution of dry pentane. It is preferable to carry-out this precipitation step in a glove box under an argon atmosphere. After the addition of about 10 ml of the tag-phosphoramidite solution, the precipitate was allowed to settle-down. The pentane (supernatant) was carefully decanted-off and was replenished with fresh pentane followed by addition of remaining tag-phosphoramidite solution. After the complete addition of the tag-phosphoramidite solution, the precipitate was stirred in pentane solution for half an hour more. The supernatant was decanted carefully, and the traces of solvent were removed under vacuum. The final product was an amorphous powder, and it was extensively dried under vacuum. The product was characterized by $^{31}$P-nmr spectroscopy. The yield of the phosphitylation reaction after the precipitation step has been consistently found to be >75%.

The tag-phosphoramidite was characterized by $^{31}$P-nmr. The sample was prepared by dissolving 45.0 mg of tag-phosphoramidite in 500 μl of $CD_3CN$. The spectrum was recorded on a JEOL 270 MHz Ft-nmr instrument with 85% phosphoric acid as the external standard.

¹H-NMR spectral data of tag-phosphoramidite: ¹H-NMR ($CD_3CN$), δ1.10–1.21(m,12); 1.61–1.72(m,2); 1.76–1.85(m, 2); 2.1(s,3 Ar—$CH_3$); 2.62–2.68(t,2); 2.82–2.88(t,2); 3.52–3.83(m,6); 7.25–7.30(m,2, 5' Ar—H); 7.39–7.46(m,4, 4 Ar—H), 7.55–7.61(m,2, 3' Ar—H); 7.75–7.80(m,4, 3 Ar—H); 8.03–8.12(m,4, 5 Ar—H); 8.39–8.45(d,2, 6' Ar—H) and 8.51–8.56,d,4, 6 Ar—H).

EXAMPLE II

Oligonucleotide synthesis

The oligonucleotides were made on an Applied Biosystems (San Jose, California) automated oligonucleotide synthesizer using the β-cyanoethyl phosphoramidite chemistry (1).

Oligonucleotide amino modifications to the 5' end occurred at the last coupling step, and at the 3' end by using a modified solid phase (controlled pore glass). Clontech (San Diego, Calif.) supplied the amino modifiers. The resulting 5' modified oligonucleotides all contain a six carbon spacer arm to the amino group designated (C6, NH2). The 3' modified oligonucleotides all contain a three carbon spacer to the amino group. Some of the sequences were labeled directly during synthesis using the tag-phosphoramidite. Oligonucleotide Ru(II) modifications to the 5' end occurred at the last coupling step using the tag-phosphoramidite (0.4M) on the Applied Biosystems automated oligonucleotide synthesizer, designated as Ru(II): in the following oligonucleotide. The oligonucleotides which were constructed, their modifications and utility are described below.

A. Oligonucleotides INFG2 (SEQ ID NO:1) and INFG3 (SEQ ID NO:2) for amplification of the human interferon gamma gene (2).

INFG2 (C6, NH2) CTCCACACTCTTTTGGATGCTCTG-GTCATC;

INFG3 (C6, NH2) CACATCATCCTCTGTTTGT-GCTCTTTCCT.

B. Oligonucleotides for human papilloma virus (HPV) directed to the E6 region (3), oligonucleotide sequences 2PV16 (SEQ ID No:3), 3PV16 (SEQ ID NO:4), 3PV16p (SEQ ID NO:4), 2PV18 (SEQ ID NO:5), 3PV18 (8EQ ID No:6).

For HPV16:

2PV16 5' (C6, NH2) CAGTTAATACACCTAATTAA-CAAATCACAC;

3PV16 5' (C6, NH2) ACAACATTAGAACAGCAATA-CAACAAACCG; and

3PV16p 5' Ru(II):ACAACATTAGAACAGCAATACAA-CAAACCG.

For HPV18:

2PV18 5' (C6, NH2) CACCGCAGGCACCTTAT-TAATAAATTGTAT;

3PV18 5' (C6, NH2) GACACATTGGAAAAACTAAC-TAACACTGGG.

These oligonucleotides enable the amplification of the fragments 3PV16 or 3PV18 for HPV 16 and 18 DNA respectively, with biotinylated 2PV16 or 2PV18 for capture of the respective amplified products.

C. Oligonucleotides for Lambda sequences, lambda 1 (SEQ ID NO:7), lambda (SEQ ID NO:7), lambda C (SEQ ID No:8), lambda 1C (SEQ ID NO:8).

lambda 1 5' Ru(II):GAAAATGTGCTGACCGGACAT-GAAAATGAG lambda 5' GAAAATGTGCTGACCGGACATGAAAAT-GAG lambda C 5' CTCATTTTCATGTCCGGTCAGCA-CATTTTC lambda 1C 5' (C6, NH2)CTCATTTTCATGTCCGGTCAGCACATTTTC D. Nonspecific oligonucleotide sequence, 2PV6 (SEQ ID NO:9).

PV6 (C6,NH2) TTTGTGACACAGGTAGCACCGAATT-AGCAC

E. Oligonucleotides for HIV sequences, SK38 (SEQ ID NO:10), SK39 (SEQ ID NO:11), and SK19 (SEQ ID NO:12).

For HIV1;

SK38 5' ATAATCCACCTATCCCAGTGGAGAAAT

SK39 5' (C6, NH2) TTTGGTCCTTGTCTTATGTCCA-GAATGC

SK19 5'
Ru(II):ATCCTGGGATTAAATAAAATAG-TAAGAATGTATAGCCCTAC

EXAMPLE III

Labeling Oligonucleotides

All the synthetic oligonucleotides were purified to remove any contaminating amino groups by gel filtration on a BIOGEL™ P6 (Bio-Rad Labs, Richmond, Calif.) column.

Biotin was introduced via the 5'-amino group of the oligonucleotides using NHS-biotin (Clontech, San Diego, Calif.). Tag-NHS ester label (an NHS ester of the Ru tris bipyridyl complex) was introduced via the amino group of the modified oligonucleotides as follows. The oligonucleotides (0.1 μmole) in 100 μl of PBS (pH 7.4) were reacted with 0.5 μmole of tag-NHS ester label dissolved in DMSO overnight at room temperature in the dark. Oligonucleotides were recovered from these labeling reactions by ethanol precipitation.

EXAMPLE IV

Characterization of Tag-phosphoramidite Labeled Oligonucleotides

The phosphoramidite labeled oligonucleotides have been characterized by high pressure liquid chromatography (HPLC). The buffer system used in the chromatography was comprised of a the following solutions: A) 100 mM triethylammonium acetate (TEAA) buffer, pH 7.25–7.50, and B) equal parts of 100 mM TEAA, pH 7.25–7.50 and HPLC grade acetonitrile.

The analysis was performed by an LKB HPLC system (Pharmacia LKB Biotechnology Inc., Piscataway, N.J.) equipped with an LKB 2140 rapid spectral detector, LKB 2150 HPLC pumps, an LKB 2152 LC controller, and LKB 2211 superrac fraction collector, a Gilson Model 231 (Gilson Medical Elec., Inc., Middleton, Wis.) sample injector, and a 401 Gilson diluter was used together with a Beckman C18 reverse phase column. The following gradient program was used during the analysis.
Gradient program:

| Time h:min | Flow rate | % B |
| --- | --- | --- |
| 0:00 | 0.50 | 10:00 |
| 0:30 | 0.50 | 40:00 |
| 0:35 | 0.50 | 10:00 |
| 0:40 | 0.50 | 10:00 |

Under the chromatographic conditions described above, the unlabeled oligonucleotides elute between 16–20 minutes, and the labeled oligonucleotides elute between 29–33 minutes. The integration of the peaks indicates that the percent of labeled oligonucleotide was greater than 80% based on absorbance at 260 nm of the eluted peak relative to unlabeled oligonucleotide.

EXAMPLE V

Gel Electrophoresis of Oligonucleotides

Samples of the phosphoramidite labeled oligonucleotides were prepared by mixing a sample (2–3 μl) with deionized formamide (3–5 μl) prior to loading on the gel. Four μg of oligonucleotide were run per sample using at least 1½ volumes of formamide per volume of oligonucleotide. These samples of oligonucleotide were analyzed on 12% polyacrylamide gels with urea prepared by standard methods (Maniatis et al., *MOLECULAR CLONING, A LABORATORY MANUAL* Cold Spring Harbor Laboratory, 1982, Cold Spring Harbor, N.Y.). Gels were run until the bromophenol blue marker dye runs to the bottom of the gel. The oligonuceotides were analyzed by placing gel (after electrophoresis was completed) on top of a fluorescent thin-layer chromatography sheet (Kodak, Cat. No. 13181.) (This is silica gel with fluorescent indicator or equivalent, Kodak, Rochester, N.Y.). The gel on the fluorescent thin-layer chromatography sheet was then illuminated with ultraviolet (UV) light (approximately 300 nm). The presence of oligonucleotide was identified by the dark bands seen due to absorption of the UV light reducing the fluorescence from the fluorescent thin-layer chromatography sheet. The molecular species produced during automated DNA synthesis are determined by analyzing photographs which record the positions and intensity of the resulting banding. The gels were also analyzed by illumination on a UV transilluminator (Fotodyne, New Berlin, Wis., Model No. 3–3000) to identify the Ru (II) complex labeled bands. The oligonuncleotides labeled with the Ru (II) complex fluoresce with a characteristic orange color which is easy to photograph. The separation and analysis of the Ru (II) labeled bands exploited the slower mobility of the Ru (II) complex labeled oligonucleotides as compared to that of the unlabeled oligonucleotides. The slower mobility of the Ru (II) complex labeled oligonucleotide results from the combination of the increased molecular weight and altered charge to mass ratio due to the presence of the Ru (II) moiety (characterized by its $2^+$ charge) as compared to the unlabeled oligonucleotide.

EXAMPLE VI

Characterization of the Labeled Oligonucleotides

The analysis of the labeled oligonucleotides by gel electrophoresis (Ex. V) demonstrated that the two phosphoramidites generated (having a 7 carbon and 4 carbon spacer respectively) (Ex.I) were able to couple efficiently during automated DNA synthesis. This was evidenced by the small amount of unlabeled material (less than 5%) detectable on these gels. The electrochemical activity of the oligonucleotides labeled using this chemistry was studied for oligonucleotides labeled with both phosphoramidites (Ex. I). The results of this study indicated that there was a 15% better signal from the 4 carbon spacer phosphoramidite (Ex. I), indicating little significant difference between the two labels.

The 4 carbon spacer phosphoramidite derivative of Ex. I (4C phosphoramidite) was selected for further characterization based upon its relative ease of synthesis. The 4C phosphoramidite of Ex. I remained active and functional on the automated synthesizer for as long as 4 days with little loss in the coupling efficiency. This 4C phosphoramidite also demonstrated a good shelf life by remaining stable for over 9 months in the dry form. The analysis of multiple batches of 4C phosphoramidite labeled oligonucleotide (Ex. I) also demonstrated the ability of the label to consistently produce identically labeled sequences. An analysis of electrochemiluminescence (ECL) properties indicated only a 3.5% coefficient of variation in the signal for 5 batches of the labeled oligonucleotide.

Further study of the stability of the labeled nucleotides under long term storage was conducted. A comparison was made of the electrochemiluminescence of four batches of oligonucleotides. Two batches which were both one week old were compared with two batches, one which was at 6 months, and one which was at 5 months, post synthesis. The comparison demonstrated only a 5.11% CV, with no indication of loss of electrochemiluminescence.

EXAMPLE VII

Preparation of Streptavidin Magnetic Beads

To 15 mg of BSA (in 2–3 ml PBS), 105 μl of dimethylsulfoxide containing 50 mg/ml of biotin-x-NHS (Clontech, San Diego, Calif.) was added followed by mixing and incubation at room temperature for 30 minutes. The reaction was stopped by adding 30 μl of 1M glycine and incubation at room temperature for 10 minutes. The reaction mix was purified by gel filtration chromatography (Bio-Gel P6, Bio-rad Labs, Richmond, Calif.). This biotin-BSA was filtered using a 0.2 μm filter and syringe. 5 mg biotin-BSA in 10 ml of 0.2M sodium carbonate/bicarbonate buffer pH 9.6 was added to 300 mg of DYNABEADS™ (DYNAL #14002) (DYNABEADS is a trademark of DYNAL, Great Neck, N.Y.) (the beads comprise either:

(i) Dynal M-450 Dynabeads, 4.5 μm diameter superparamagnetic particles, 30 mg/mL, obtained from Dynal, 45 North Station Plaza, Great Neck, N.Y. 11021; or (ii) Dynal M-280 Dynabeads, 2.8 μM diameter superparamagnetic particles, 10 mg/mL, obtained from Dynal, 45 North Station Plaza, Great Neck, N.Y. 11021)

washed with carbonate/bicarbonate. This mixture was vortexed, and incubated overnight at room temperature with mixing. The beads were magnetically separated followed by the addition of 10 ml ECL diluent (37.5 mM $KH_2PO_4$, 109.2 mM $K_2HPO_4.3H_2O$, 151.7 mM NaCl, 0.65 mM $NAN_3$, 0.43 mM bovine serum albumin in $H_2O$) and 100 μl tRNA (10 mg/ml)and 100 μl tRNA (10 mg/ml). This mixture was incubated for 3–4 hours at room temperature with mixing. The beads were washed once with 10 ml of ECL diluent and resuspended in 10 ml of ECL diluent and 100 μl tRNA (10 mg/ml). This mixture was mixed and incubated at 2°–6 ° C. overnight to stabilize proteins on beads. The beads were magnetically separated and suspended in 10 ml of phosphate buffered saline (PBS) containing 15 mg of streptavidin (Scripps Laboratories, San Diego, Calif., catalog number S1214) followed by mixing for one hour. The beads were washed 4 times in 10 ml ECL diluent, with 5 minutes mixing for each wash. The beads were finally resuspended in 29.7 ml of ECL diluent and 300 μl tRNA (10mg/ml) to a final concentration of 10 mg/ml particles+100 μg/ml tRNA.

EXAMPLE VIII

Amplification of Human Interferon Gamma Gene

A. Amplification procedure.

The amplification reaction was set up as follows. A reaction mixture was prepared containing dATP 200 μM, dCTP 200 μM, dGTP 200 μM, dTTP 200 μM, $MgCl_2$ 2 mM, Tris-HCL 10 mM, pH 8.3, 50 mM KCl, Primer 0.5 μM, AmpliTaq® (Perkin Elmer-Cetus, Norwalk, Conn.) 40Units/ml and sample DNA 1 μg. The primer used was the INFG3 primer (Ex. IIA) labeled with tag-NHS ester. The DNA samples were human placental DNA (Sigma, St. Louis, Mo.) and Salmon sperm (SS) DNA (Sigma) as the control. This reaction mix was subjected to 80 cycles of 97° C. for 10 sec and 50° C. for 1 sec in a Perkin Elmer-Cetus DNA thermal cycler. The samples were analyzed for amplification by hybridization with 2 ng of INFG2 (SEQ ID NO:1) labeled with biotin to 90 μl of sample for 30 min at 55° C. These hybridized samples were then incubated with 20 μg of streptavidin beads for 30 min at room temperature with shaking to capture the biotinylated probe. These beads were then washed three times with ECL assay buffer (112 mM $KH_2PO_4$, 88 mM $K_2HPO_4.3H_2O$, 50 μM NaCl, 6.5 mM $NAN_3$, 0.8 μM TRITON X-100 surfactant, 0.4 mM TWEEN 20 buffer, 100 mM tripropylamine) and the samples of beads resuspended in ECL assay buffer and read on an ECL analyzer to determine the level of electrochemiluminescence (ECL) expressed as numbers of ECL counts. The result was as follows: for the salmon sperm DNA, 62 counts; and for the human placental DNA, 22961 counts. This result demonstrated the specific amplification of the interferon gene segment of interest.

B. Evaluation of Amplification by Southern Blot.

In order to evaluate the nature of this amplification, a Southern blot analysis was performed upon amplified product. Ten μl of the INFG3 (SEQ ID NO:2) amplified human DNA sample (equivalent to 100 ng of starting DNA), 10 μl of INFG3 (SEQ ID NO:2) amplified salmon sperm DNA, 1 μg of human placental DNA and DNA size markers were subjected to gel electrophoresis followed by transfer to nitrocellulose membrane (4). This blotted DNA was then subjected to hybridization with the INFG2 (SEQ ID NO:1) biotinylated probe followed by detection using a streptavidin alkaline phosphatase kit following recommended procedures (Life Technologies, Gaithersburg, Md.). The result of this test was the demonstration of two strongly hybridizing species in the amplified sample. These species were estimated based on the DNA size markers to be of 620 and 590 base pairs. As expected the unamplified human DNA did not show any signal nor did the salmon sperm amplified controls. This data from the Southern blot analysis supports the conclusion from the ECL assay that single primer amplification was observed.

EXAMPLE IX

Amplification of Human Papilloma Virus 16 (HPV16) DNA

A. Amplification procedure.

The amplification reaction was set up as follows. A reaction mixture was prepared containing dATP 200 μM, dCTP 200 μM, dGTP 200 μM, dTTP 200 μM, $MgCl_2$ mM, Tris-HCL 10 mM, pH 8.3, 50 mM KCl, Primer 0.5 μM, AmpliTaq® (Perkin Elmer-Cetus) 40Units/ml and sample DNA 1 μg. The primer used was the 3PV16 (SEQ ID NO:4) primer labeled with tag-NHS ester. The DNA samples were HPV16 DNA (5) and Salmon sperm DNA (Sigma) as the control. This reaction mixture was subjected to 80 cycles of 97° C. for 10 sec and 50° C. for 1 sec in a Perkin Elmer-Cetus DNA thermal cycler.

The samples were analyzed for amplification by hybridization with 2 ng of 2PV16 labeled with biotin to 90 μl of sample for 30 min at 55° C. These hybridized samples were then incubated with 20 μg of streptavidin beads for 30 min at room temperature with shaking to capture the biotinylated probe. These beads were then washed three times with ECL assay buffer and the samples of beads resuspended in ECL assay buffer and read on an ECL analyzer to determine the level of ECL. The result was as follows expressed in ECL counts: for the salmon sperm DNA, 67 counts; and for the HPV16 DNA, 32444 counts. This result demonstrated the specific amplification of the HPV16 DNA of interest.

B. Evaluation of Amplification by Southern Blot.

In order to evaluate the nature of this amplification, a Southern blot analysis was performed. Ten μl of the 3PV16 amplified HPV16 DNA sample (equivalent to 100ng of starting DNA), 10 μl of 3PV16 amplified salmon sperm DNA, 1 μg of HPV16 DNA and DNA size markers were subjected to gel electrophoresis followed by transfer to nitrocellulose membrane (5). This blotted DNA was then subjected to hybridization with the 2PV16 biotinylated probe followed by detection using streptavidin alkaline phosphatase kit following recommended procedures (Life Technologies, Gaithersburg, Md.). The result of this test was the demonstration of a strongly hybridizing species in the amplified HPV16 DNA sample. This species was estimated, based on the DNA size markers, to be 870 base pairs. The unamplified HPV16 DNA did not show any signal nor did the salmon sperm amplified controls. This data from the southern blot analysis supports the conclusion based on ECL assay evidence that single primer amplification was achieved.

EXAMPLE X

Time Course of Amplification

Samples of human placental HPV 16 (CaSki) and HPV18 (HeLa) DNA were subjected to amplification as described above using INFG3 (SEQ ID NO:2), 3PV16p (SEQ ID NO:4) (ECL labeled using the tag-phosphoramidite) and 3PV18 (SEQ ID NO:6) respectively, but samples were removed at cycle numbers 20, 30, 40, 50, 60, and 80. These samples were then analyzed to determine the level of the amplified product as indicated by ECL counts.

TABLE 1

| ECL Results. | Cycle Number | | | | | |
|---|---|---|---|---|---|---|
| Primer/DNA | 20 | 30 | 40 | 50 | 60 | 80 |
| 3PV16p/HPV16 | 72 | 262 | 5234 | 10879 | 7708 | 6662 |
| SS* | — | — | — | — | — | 84 |
| 3PV18/HPV18 | 370 | 583 | 1756 | 6857 | 6794 | 6073 |
| SS | — | — | — | — | — | 148 |
| INFG3/Human | 85 | 53 | 199 | 2785 | 3533 | 5491 |
| SS | — | — | — | — | — | 86 |

*SS = salmon sperm

These results demonstrated that the amplification was occurring by an unexpected method as the levels of the signal generated showed rapid amplification after cycle 30, demonstrating an exponential amplification. This amplification using 3PV16p (SEQ ID NO:4) demonstrated the ability of phosphoramidite labeled oligonucleotide to replace the tag-NHS ester labeled oligonucleotide in a single primer amplification.

EXAMPLE XI

Optimal Temperature for Amplification

To study the effect of differing temperature cycles on the amplification, different temperature cycles were evaluated. The lower temperature of the two step cycle was varied. The cycle temperatures were 97° C. to 30° C., 97° C. to 40° C., 97° C. to 50° C., 97° C. to 60° C. and 97° C. to 70° C. These cycles are thus referred to by the lower temperature for clarity. In addition, the Ericomp (Twin Block, Ericomp Inc, San Diego, Calif.) thermocycler was used. The other conditions for amplification were as described for the time course above for human interferon and human papilloma virus DNA.

TABLE 2

A. Results with the Perkin Elmer DNA thermal cycler.

| Primer | DNA | Cycle Lower Temperature | | | | |
|---|---|---|---|---|---|---|
| | | 30° C. | 40° C. | 50° C. | 60° C. | 70° C. |
| 3PV16p | HPV16 | 10103 | 16791 | 10579 | 12266 | 61 |
| | SS | 89 | 113 | 130 | 92 | 65 |
| 3PV18 | HPV18 | 50 | 113 | 5595 | 96 | 62 |

TABLE 2-continued

A. Results with the Perkin Elmer DNA thermal cycler.

| Primer | DNA | Cycle Lower Temperature | | | | |
|---|---|---|---|---|---|---|
| | | 30° C. | 40° C. | 50° C. | 60° C. | 70° C. |
| | SS | 73 | 86 | 134 | 125 | 66 |
| INFG3 | Human | 101 | 1348 | 7119 | 6390 | 52 |
| | SS | 63 | 81 | 220 | 917 | 41 |

TABLE 3

B. Results with the Ericomp thermal cycler.

| Primer | DNA | Cycle Lower Temperature | | | | |
|---|---|---|---|---|---|---|
| | | 30° C. | 40° C. | 50° C. | 60° C. | 70° C. |
| 3PV16p | HPV16 | 16307 | 10491 | 9093 | 16346 | 71 |
| | SS | 66 | 106 | 94 | 103 | 66 |
| 3PVI8 | HPV18 | 204 | 699 | 8388 | 4731 | 76 |
| | SS | 50 | 51 | 86 | 70 | 73 |
| INFG3 | Human | 190 | 3436 | 6350 | 6617 | 46 |
| | SS | 70 | 72 | 1265 | 993 | 56 |

These results demonstrate the temperature dependent nature of this amplification reaction and indicate the need for optimization of temperatures to allow amplification with certain templates as each particular template-primer combination has a different temperature optimum. The skilled artisan will understand that temperature optimization is often necessary in developing an amplification procedure. This single primer amplification temperature study demonstrated the ability of the phosphoramidite labeled oligonucleotide to withstand the high temperatures and long incubation times in this single primer amplification.

EXAMPLE XII

Amplification Using Differing DNA Polymerase Enzymes

DNA polymerase from differing sources was tested to establish that single primer amplification is not enzyme specific.

Reaction mixtures were prepared consisting of the following compositions.

REPLINASE™ polymerase (DuPont, Boston Mass.); 50 mM Tris-HCl, pH 9.0, 20 mM ammonium sulfate, 1.5 mM $MgCl_2$, dATP 200 μM, dCTP 200 μM, dGTP 200 μM, dTTP 200 μM, Primer 0.5 μM, 10 μg/ml sample DNA, 40Units/ml REPLINASE™.

HOT TUB™ DNA polymerase (Amersham, Arlington Heights, Ill.); 25 mM Tris-HCl, pH 9.5 (25° C.), 50 mM KCl, 10 mM $MgCl_2$, 1 mg/ml bovine serum albumin (BSA), dATP 200 μM, dCTP 200 μM, dGTP 200 μM, dTTP 200 μM, 0.5 μM primer, 10 μg/ml sample DNA, 40Units/ml HOT TUB™ DNA polymerase: PYROSTASE™ polymerase (Molecular Genetic Resources, Tampa, Fla.); dATP 200 μM, dCTP 200 μM, dGTP 200 μM, dTTP 200 μM, 50 mM Tris-HCl pH 9.0(25° C.) 15 mM $MgCl_2$, 20 mM ammonium sulfate, 0.01% gelatin, Primer 0.5 μM, 10 μg/ml sample DNA, 40Units/ml PYROSTASE™: VENT™ DNA polymerase (New England Biolabs, Beverly, Mass.); dATP 200 μM, dCTP 200 μM, dGTP 200 μM, dTTP 200 μM, 20 mM Tris-HCl, pH 8.8, 2 mM $MgSO_4$, 10 mM ammonium sulfate, 10 mM KCl, 0.1% TRITON X-100 surfactant, 0.1 mg/ml BSA, 0.5 µM primer, 10 µg/ml sample DNA, 40Units/ml VENT™ DNA polymerase: AMPLITAQ® (Perkin Elmer-Cetus) under the conditions described above.

These polymerases were used to amplify samples of HPV16 (CaSki) DNA using primer 3PV16 (SEQ ID NO:4), and human placental DNA using primer INFG3 (SEQ ID NO:2). Samples of 100 µl were cycled in the Perkin Elmer-Cetus Thermal cycler using a cycle of 97° C. 10 sec and 50° C. 1 sec for 80 cycles. The HPV and human interferon gamma amplified products were analyzed as above.

ECL assay of amplification products, expressed as ECL counts, are as follows:

TABLE 4

| Primer/DNA | DNA polymerase | | | | |
|---|---|---|---|---|---|
| | AM-PLITAQ | HOT TUB | VENT | PYRO-STASE | REPLI-NASE |
| 3PV16p/HPV16 | 7449 | 9266 | 209 | 7976 | 6935 |
| INFG3/Human | 5304 | 5570 | 262 | 5599 | 5581 |

These results demonstrate that most DNA polymerases would work with this amplification system with very little optimization of Mg++ or temperature conditions. The poor activity from the Vent DNA polymerase may be due to non-optimal Mg++ conditions. This demonstration, that the phosphoramidite labeled oligonucleotide is able to direct single primer amplification with a wide range of DNA polymerases, indicates that it does not inhibit these reactions.

EXAMPLE XIII

Sensitivity of Amplification

Samples of DNA were diluted and subjected to the single amplification as described above using Taq polymerase. The samples were assayed as described above using the biotinylated primers INFG2 (SEQ ID NO:1), 2PV18 (SEQ ID NO:5) and 2PV16 (SEQ ID NO:3). The results are expressed as ECL counts.

TABLE 5

| DNA Amount of DNA, ng | Tag labeled primers | | | | | |
|---|---|---|---|---|---|---|
| | INFG3 Human | SS | 3PV18 HPV18 | SS | 3PV16p HPV16 | SS |
| 1000 | 13150 | 112 | 1366 | 332 | 12279 | 114 |
| 500 | 12347 | — | 5157 | — | 11895 | — |
| 250 | 12807 | — | 5319 | — | 11717 | — |
| 25 | 7272 | — | 2441 | — | 11121 | — |
| 1 | 2037 | — | 580 | — | 12038 | — |

These results demonstrate the sensitivity of this method. The human interferon gene was detected in only 1 ng of sample DNA. These results are consistent with the data for the HPV DNA samples (Hela and CaSki of Example X). The result from the control sample of 1 µg of salmon sperm DNA demonstrates the specificity of this assay system. This demonstrates the utility of the method for diagnosis and detection of specific genes from small sample sizes. The ability of the phosphoramidite labeled primer to undergo single primer amplification efficiently enables the detection of HPV16 in 1 ng of DNA.

EXAMPLE XIV

Optimal Primer Concentration

Preliminary studies were performed utilizing HOT TUB™, PYROSTASE™ and REPLINASE™ (isolated from *Thermus flavis*) polymerases which provided the best results in the previous examples, to determine optimal primer concentrations. Concentrations of 200 ng per 100 µl reaction (0.2 µM) or lower were ineffective. The optimal concentration was about 500 ng per 100 µl reaction (0.5 µM). Above 0.5 µM little improvement was evident. In particular, the PYROSTASE™ and the REPLINAS™ demonstrated better response in comparison to the other polymerases tested during the initial primer study and hence were characterized further. The results from these studies with the tag-phosphoramidite label INFG3 (SEQ ID NO:2) primer and INFG2 (SEQ ID NO:1) biotinylated probe are illustrated below in TABLE 6. The results are expressed as ECL counts.

TABLE 6

| Amount of primer per reaction | Polymerase: | | | |
|---|---|---|---|---|
| | PYROSTASE ™ | | REPLINASE ™ | |
| | DNA sample | | | |
| | Human | SS | Human | SS |
| 2 µg | 10522 | 658 | 6597 | 181 |
| 500 ng | 4490 | 132 | 4509 | 225 |
| 200 ng | 227 | 66 | 172 | 65 |

These results demonstrate a broad optimal concentration range for the primers. The lower concentration of 500 ng per 100 µl appears to be best suited to the ORIGEN™ assay system as the background levels tend to be lower and the use of oligonucleotide is more economical. Other assay systems and cloning methods would be expected to have differing optimal concentrations but would generally be expected to follow these values indicated here. The results of this example assay indicated that PYROSTASE™ provided the best results due to its ability to function well at low and at high primer concentrations.

EXAMPLE XV

Amplification of Human Papilloma Virus (HPV18) DNA

Oligonucleotide 3PV18 (SEQ ID NO:6) was used to amplify 1 µg of HPV18-containing DNA (Hela) and a control containing salmon sperm DNA, using the protocol described earlier with Taq and with cycling from 97° C. to 60° C. in the Ericomp thermocycler. These amplified samples (10 µl i.e. 10% of the amplified sample) were run on a 1% agarose gel together with 1 µg of unamplified material and molecular weight markers. This material was then Southern blotted using known methods and hybridized with a $^{35}$S labeled 2PV18 probe. This probe (as described in Example IIB) has an amino group and was labeled using Amersham's '$^{35}$S labeling reagent' (Amersham, Arlington Heights, Ill.). In brief, 2.5 µg of oligonucleotide was taken and reacted with 50 µCi of the '$^{35}$S labeling reagent' in 10 µl of 80% DMSO overnight. This labeled probe was precipitated from 70% ethanol and washed. The probe was resuspended in 500 µl of hybridization buffer and used at the concentration of $2.5 \times 10^6$ counts per 5ml of hybridization solution. The filters were hybridized at 55° C. in 6XSSC, 0.5% SDS, 10 mM EDTA[3] then washed in 0.16XSSC, 0.1% SDS at 60° C. and dried. The filters were next sprayed with ENHANCE™ spray (NEN, Boston, Mass.) and placed under film. The result of this hybridization experiment was the detection of specific products from the single primer amplification of the HPV18 containing DNA. The estimated size of the major product was determined to be about 2000 bases in light of the molecular weight standards used. The other samples did not demonstrate any hybridization even though 10 fold more material was loaded of the unamplifiied material. This demonstrated the ability of the single primer amplification to amplify a single species.

EXAMPLE XVI

Paired Primer Polymerase Chain Reactions

Paired primer polymerase chain reaction's (PCR) were performed essentially as described (6, 7). Reactions were typically of 100 µl unless otherwise stated. PCR was carried out in the asymmetric mode, using 5 pmoles of the SK38 (SEQ ID NO:10) oligonucleotide and 50 pmoles of SK39 (SEQ ID NO:11) (biotinylated) oligonucleotide or in the standard mode using 50 pmoles of both SK38 (SEQ ID NO:10) and SK39 (SEQ ID NO:11).

The thermocycler conditions were as follows: 95° C. for 1 min followed by 60° C. for 1 min. The cycle numbers for these PCR runs were 30 for the separation assay and 40 for the non-separation assay or for the detection of less than ten copies of HIV.

EXAMPLE XVII

Hybridization Studies

Melting studies using the hypochromic shift at 260 nm were carried out on a Hitachi U3200 (Hitachi Instruments, Inc., Danbury, Conn.) dual wavelength spectrophotometer and its temperature controlled cell. The samples of lambda hybridized to lambda C (SEQ ID NO:8) (1.64 mM) and lambda 1 (SEQ ID NO:7) (Tag labeled) hybridized to lambda C (SEQ ID NO:8) (1.05 mM) in 500 mM NaCl, 10 mM Tris-HCl pH 7.4 were introduced into matched cuvettes blanked and heated at 1° C. per minute with 500 mM NaCl, 10 mM Tris-HCl pH 7.4 as the control sample. This assay was repeated three times and the data averaged, normalized and corrected for the Tag label absorption between the two samples.

Melting studies on beads were carried out on preformed hybrids of either lambda 32p or lambda 1 (SEQ ID NO:7) (Tag label) and lambda 1C (SEQ ID NO:8) (biotinylated). Hybrids were formed by hybridization of 114 pmoles of either lambda 32p or lambda 1 (SEQ ID NO:7) (Tag label) with 60 pmoles of lambda 1 C (SEQ ID NO:8) (biotinylated) at 50° C. for 20min. These complexes were captured on 1.5 mg of streptavidin beads (Ex. VII). Beads with the bound hybrids were aliquoted out at 50 µg (500 µl) per assay and incubated at various temperatures for 5min with shaking followed by separation on a magnetic rack and washed into fresh ECL assay buffer. The bead bound signal was determined for the respective samples (in triplicate) by analysis in a Beckman LS-100C (Beckman, Irvine, Calif. 92664) liquid scintillation counter or an ECL apparatus. The results were normalized to the signal from the $^{32}$P results to allow a comparison of the data. The data for the 3 hour time point was used as the reference point for normalizations.

Studies of the kinetics of hybridization were performed using pre-captured lambda 1C, (SEQ ID NO:8) (biotinylated) on beads (0.1 pmole on 80 µg of beads per assay). Lambda 1 (Tag label) or lambda ($^{32}$P labeled) were added (0.3 pmoles per assay) in 500 µl of ECL assay buffer. Samples were incubated for various times with a 3 hr time point used as the 100% hybridized sample for the normalization of sample signals. After hybridization, the hybrid was separated from the unhybridized probe using a magnetic rack and the supernatant was removed. These samples were resuspended in 600 µl of ECL assay buffer and analyzed on an ECL apparatus or in a Beckman LS-100C liquid scintillation counter depending on the sample. Samples were run in triplicate and the data background subtracted and normalized to the signal from the lambda ($^{32}$p labeled) samples hybridized for 3 hours.

The test assay format for a comparison of Tag label and $^{32}$P labeled probes consisted of a standard curve representing a range of concentration ratios of biotinylated 2PV6, (SEQ ID NO:9) and biotinylated lambda 1C mixtures to yield a constant concentration of 6 pmoles of oligonucleotide per assay. The standard curve was constructed by preparing an assay medium having lambda 1C (target) in the ranges of: 0.0, 1.25, 1.5, and 3 pmoles/sample. This standard curve was designed to mimic the concentrations of product from a PCR reaction, in which differing levels of biotinylated PCR product must be measured against a constant background of biotinylated primer. In addition to this standard curve, a set of control samples was prepared in the same way containing 0.0, 0.333, 0.167, 0.600, 1.67, 0.866, 3.00, 2.17, 1.33, 3.50 pmoles of biotinylated lambda 1C (SEQ ID NO:8) (15 µl) together with a biotinylated oligonucleotide at a constant amount of 6 pmoles/sample. These standards and controls were then subjected to analysis using 500 µg (50 µl) of streptavidin beads in ECL assay buffer for capture by incubation with shaking at room temperature for 15 min. The solid phase was separated using magnetic racks and the captured oligonucleotides were then subjected to a wash with 0.05M NaOH to mimic the wash used for PCR samples. The beads were then washed into the ECL assay buffer followed by the addition of 6 pmoles (6 µl) of either the lambda 1 (containing the Tag label) or lambda $^{32}$P labeled (0.2 µCi) probe. These were hybridized for 15 min. at 50° C., followed by washing twice in ECL assay buffer for (500 µl) the Tag label assays or four times for the $^{32}$P label assays. These samples were either analyzed on an ECL apparatus or counted on a Beckman LS-100C liquid scintillation counter. These assay runs were carried out three times for each label, with each sample or standard within a run measured in triplicate.

EXAMPLE XVIII

Paired Primer PCR HIV DNA Assays

Paired primer PCR amplifications of HIV1 gag gene were carried out using oligonucleotides SK38 (SEQ ID NO:10) and SK39 (SEQ ID NO:11). Using biotinylated SK39 with unlabeled SK38, the resulting PCR product was hybridized to Tag label probe SK19 as described above.

For the non-separation assay, an asymmetric PCR reaction was performed with an excess of the biotinylated primer. This PCR reaction generated an excess of biotinylated single-stranded DNAs now available for direct hybridization by the Tag labeled probes. For hybridization, 1 pmole of Tag-oligonucleotide SK19 (SEQ ID NO:12)(50 µl), specific for the HIV1 gag gene to be amplified, was added to 15

μl of the PCR after amplification, followed by incubation for 15 min. at 60° C. To this hybridization mixture was added 60 μl of ECL assay buffer containing 600 μg of streptavidin coupled beads, and then the mixture was incubated with shaking at room temperature for 15 min. The sample volume was increased to 600 μl by addition of ECL assay buffer, followed by detection of electrochemiluminescence with an ECL apparatus.

The quantitative assay protocol was performed as follows: standards of 0, 50, 100, 400, 2000 copies of HIV1 (Perkin Elmer Cetus, Norwalk, Conn.) per PCR were run in triplicate. From the PCR, three 15 μl aliquots of the reaction mixture were added to 600 μg of streptavidin coupled beads followed by incubation at room temperature for 15 min. The solid phase in these samples was separated using magnetic racks, washed with 50 mM NaOH, washed with ECL assay buffer and resuspended in 100 μl of ECL assay buffer containing 10 pmoles of the labeled oligonucleotide SK19 (SEQ ID NO:12). These samples were hybridized for 15 min. at 60° C. The solid phase was separated using magnetic racks, washed with ECL assay buffer three times, resuspended in 600 μl ECL assay buffer and electrochemiluminescence detected by an ECL apparatus. Each sample and standard were run in triplicate.

EXAMPLE XIX

Advantages of the Ru (II)—Phosphoramidite Label

The effectiveness of the tag-phosphoramidite label

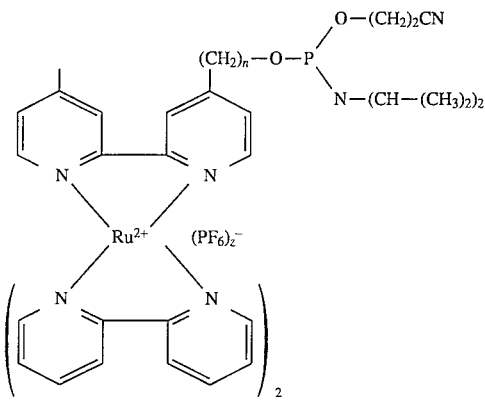

was tested by the synthesis of a test sequence lambda 1 (SEQ ID NO:8). This labeled sequence was analyzed by gel electrophoresis and by HPLC of the labeled and unlabeled DNA. This analysis demonstrated greater than 90% coupling efficiency may be obtained with this phosphoramidite. Comparison of five batches of labeled lambda 1 sequence demonstrated very little variation in the recovered ECL counts per mole of oligonucleotide.

To determine the effect that these labels would have on hybridization kinetics and melting curves, the following studies were performed:

A. Denaturation of the DNA Complexes by Temperature

Denaturation of the DNA complexes by temperature was monitored by the hypochromic shift seen with denaturing (1). To confirm this data on the denaturation temperature profile, the denaturation of preformed hybrids from the surface of ECL assay beads cin comparison to a $^{32}P$ assay, was analyzed. These data demonstrate that the denaturing temperature profile for these sequences were virtually identical.

B. Effects of Tag-Phosphoramidite ECL Label on Hybridization Kinetics

Studies into the kinetics of hybridization in the presence of the tag-phosphoramidite ECL label were initially hampered by the rapid rate (less than one minute) of hybridization with the utilized assay format.

The concentration of the probe was reduced by dilution to provide a slower rate of hybridization to the bead bound target in order to increase the accuracy of the resulting measurements.

C. Comparison of ECL Taq-phosphoramidite Assay to $^{32}P$ Assay

Studies of the kinetics of hybridization also demonstrated that the addition of the tag-phosphoramidite label had little effect on the kinetics of probe hybridization, with the rates for both Ru (II) labeled probe (tag-phosphoramidite) and $^{32}P$ probes being identical. This information combined with the denaturation results indicates that in most cases the kinetic properties of these synthetically labeled oligonucletides will be identical to that of the native sequences.

The behavior of the tag-phosphoramidite labeled oligonucletide (as a probe) in an assay environment was compared to that of a reference assay comprising $^{32}P$ labeled oligonucleotides. A set of standards and a set of samples from dilutions of a synthetic biotinylated 30 base oligonucleotide complementary to the tag-phosphoramidite labeled oligonucleotide probe were compared. Y=values determined by the ECL assay and X=values determined by $^{32}P$ assay. The data produced the following equation $Y=-3.6\times10^{-2}+0.84X$, $R^2=0.996$. The analysis of the individual samples results relative to the known value generated standard error of estimates for both the ECL (0.59) and $^{32}P$ (3.54) allowing a comparison of the relative error of these two methods.

The results of the comparison between the tag-phosphoramidite labeled oligonucleotide and a $^{32}P$ labeled probe (in a model assay) demonstrated a good correlation between these methods, with a correlation coefficient ($R^2$) of 0.996. Analysis of the standard error of estimates for both the ECL (0.59) and $^{32}P$ (3.54) samples allowed a comparison of the relative error of these two methods. This analysis demonstrated the greater precision of the ECL method using these phosphoramidite labeled oligonucleotides over the $^{32}P$ labeled probes in this assay. These differences are possibly due to the greater specificity of the ECL measurement of the bead bound Ru (II) label (tag-phosphoramidite), as the $^{32}P$ determination will measure both bead bound and any residual free label. This effect on measurements and the difficulty of handling radioisotopes both have contributed to the poor performance of the $^{32}P$ assay relative to the ECL assay of the tag-phosphoramidite labeled oligonucleotides.

D. Stability of Ru (II) Label

The stability of the Ru (II) (tag-phosphoramidite) label was demonstrated by the direct labeling of oligonucleotides using phosphoramidite chemistry. The label was subjected to oxidization by $I_2$, hydrolysis with $NH_3$ overnight at 55° C., followed by the recovery of intact and active labeled oligonucleotides. Oligonucleotides labeled in this way were analyzed by HPLC, gel electrophoresis and ECL activity and judged to be pure and active for ECL assays. This stability of the oligonucleotides under these conditions indicates that the reagents of assay kit prepared from components including oligonucleotides labeled according to the invention will be stable and provide a highly reproducible assay.

E. DNA—Ru (II) (Taq-Phosphoramidite) Interactions

Interaction of Ru (II) complexes with DNA has been described (8, 9). These interactions are known to produce effects on the binding affinity of the labeled probes for the target DNA. Enzyme and biotin labels also interfere with probe binding (PCT U.S. patent application Ser. No. 87/00987, WO87/06706, 10). These effects have been controlled by lowering the hybridization temperature and other such maneuvers. In contrast, the tag-phosphoramidite label demonstrates little, if any, effect on the binding affinity of labeled probes for DNA. This is demonstrated by the hybridization studies discussed above which clearly demonstrate that the tag-phosphoramidite labeled probes have utility without the necessity for adjustments to the assay parameters.

F. Comparison of Tag-Phosphoramidite and Tag-NHS

Tag-NHS ester was used to label oligonucleotides in examples VIII, IX, X, XI, XII, XIII, XIV and XV for comparison with tag-phosphoramidite labeled oligonucleotides. The difference between the two labeling reagents was found essentially to be in the ability of the tag-phosphoramidite to be used for automated nucleic acid synthesis and labeling procedures.

The terms and expressions which have been employed are used as terms of description and not of limitation, and there is no intention in the use of such terms or expressions of excluding any equivalents of the features shown and described, its being recognized that various modifications are possible within the scope of the invention.

REFERENCES

1. Beaucage, S. L. and Caruthers, M. H., "Deoxynucleoside phosphoramidites, a new class of key intermediates for deoxypolynucleotide synthesis", *Tetrahedron Lett.* 22, 1859–62 (1982).

2. Gray, P. W. and Goeddel, D. V., "Structure of the human immune interferon gene", *Nature* 298, 859–863 (1982).

3. Shibata, D. K., Arnheim, N. B., and Martin, J. W., "Detection of human papilloma virus in paraffin-embedded tissue using the polymerase chain reaction", *J. Exp. Med.* 167, 225–30 (1988).

4. Yee C., Krishnan-Hewlett, I., Baker C. C., Schlegel, R., and Howley, P. M., "Presence and Expression of Human Papillomavirus sequences in human cervical carcinoma cell lines", *Am. J. Pathol.* 119, 361–6 (1985).

5. Zoski, G. and Woodward, S., "Apparatus for Conducting Measurements of Electrochemiluminescent Phenomena", PCT U.S. patent application Ser. No. 89/04854 corresponding to pending EPO application 89912913.4, pub. Aug. 21, 1991, publication no. 0441880.

6. Mullis, K. B., and Faloona, F. A., "Specific synthesis of DNA in vitro via a polymerase-catalyzed chain reaction" *Methods Enzymol* 155 335–50 (1987)

7. Barone, A. D., Tang, J-Y, and Caruthers, M. H., "In situ activation of bis-dialkylaminophosphines—a new method for synthesizing deoxyoligonucleotides on polymer supports" Nucleic Acids Res. 12, 4051–61 ( 1984 ).

8. Updyke, T. V., and Nicolson, G. L., "Immunoaffinity isolation of membrane antigens with biotinyated monoclonal antibodies and streptavidinagarose", *Methods Enzymol.* 121, 717–25 (1986).

9. Cardullo, R. A., Agrawal, S., Flores, C., Zamecnik, D. C., and Wolf, D. E., "Detection of nucleic and hybridization by nonradiative fluorescence resonance energy transfer" *Proc. Natl. Acad. Sci.* 85, 8790–4 (1988).

10. Ou, C-Y, Kwok, S., Mitchell, S. W., Mack, D. H., Sninsky, J. J., Krebs, J. W., Feorino, P., Warfield, D., and Schochetman, G., "DNA amplification for direct detection of HIV-1 in DNA of peripheral blood mononuclear cells", *Science* 239, 295–97 (1988).

---

What we claim is:

1. A compound of the formula:

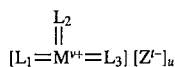

wherein M is selected from the group consisting of Ru, Os and Re; $u \cdot t = v$, u is 1 or 2 and t is 1 or 2; $L_1$, $L_2$, and $L_3$ are the same or not all the same and each is

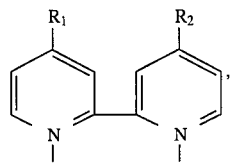

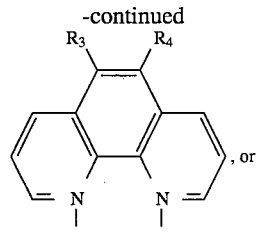

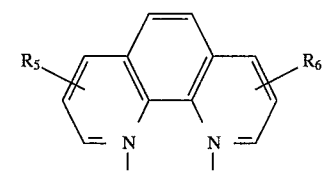

wherein $R_1$, $R_2$, $R_3$, $R_4$, $R_5$ and $R_6$ are the same or not all the same and each is H, alkyl of from 1–5 carbon atoms,

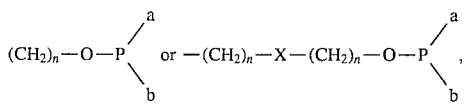

and at least one of $R_1$, $R_2$, $R_3$, $R_4$, $R_5$ and $R_6$ is either

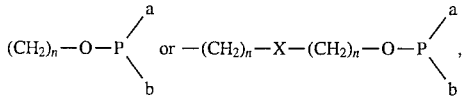

n is an integer in the range from 1–20; X is selected from the group consisting of O, S, $SO_2$, COO, and CONH; a and b are $-N(CH-(CH_3)_2)_2$, $-NH-CH-(CH_3)_2$, $O-(CH_2)_2-CN$, $O-CH_3$ or morpholino, provided that a and b are not the same; and Z is a counterion, provided that said counterion is an anion associated with the synthesis or purification of the compound; and further provided that ligands $L_1$, $L_2$ and $L_3$ are selected such that the compound is capable of electrochemiluminescence.

2. A compound as recited in claim 1 wherein $L_1$, $L_2$ and $L_3$ are all substituted or unsubstituted bipyridyl and n is from 4 to 7.

3. A compound as recited in claim 1 wherein the ratio of the relative ECL capability of the compound to the relative ECL capability of its bipyridyl analog is greater than or equal to 0.10.

4. A compound of the formula:

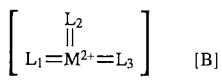

wherein M is selected from the group consisting of Ru, Os and Re; $L_1$, $L_2$ and $L_3$ are the same or different and each is

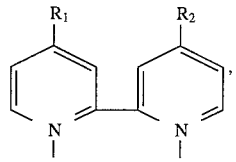

wherein $R_1$, $R_2$, $R_3$, $R_4$, $R_5$ and $R_6$ are the same or different and each is H or an alkyl group of 1–5 carbon atoms provided, however, that one of $R_1$–$R_6$ is a linker of the formula

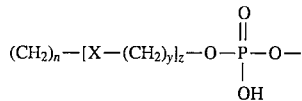

wherein n is an integer from 1–20; X is selected from the group consisting of O, S, $SO_2$, COO and CONH; y is an integer of from 1–20; z is 0 or 1; and B is a biomolecule or a synthetic analog thereof, and the phosphodiester group is bound to said biomolecule; said compound being capable of electrochemiluminescence.

5. A compound as recited in claim 4 wherein the ratio of the relative ECL capability of the compound to the relative ECL capability of its bipyridyl analog is greater than or equal to 0.10.

6. A complex of the formula

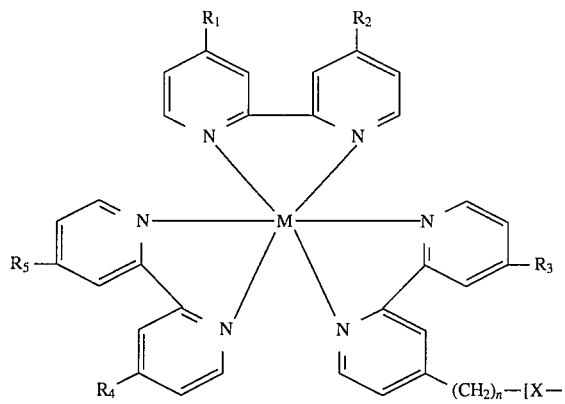
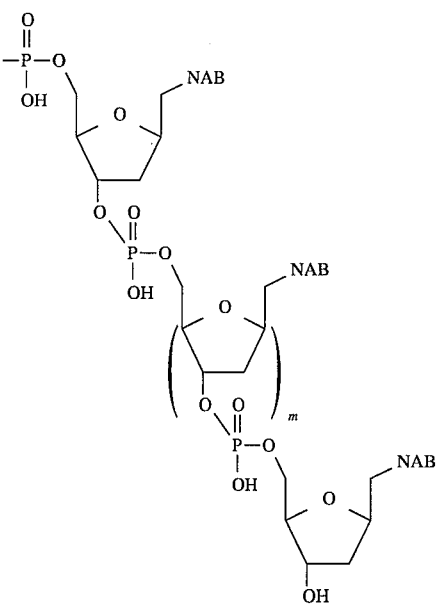

wherein M is ruthenium, osmium or rhenium; $R_1, R_2, R_3, R_4$ and $R_5$ are the same or different and each is H or alkyl of 1–4 carbon atoms; n is an integer from 1 to 20; X is selected from the group consisting of O, S, $SO_2$, COO and CONH; y is an integer of from 1–20; z is 0 or 1; m is an integer of from 1–1000; and NAB is a nucleic acid base which may be modified or unmodified; said complex being able to electrochemiluminesce.

7. A complex as recited in claim 6 wherein said nucleic acid is a primer for a polymerase amplification reaction.

8. A complex as recited in claim 6 wherein said nucleic acid is a hybridization probe.

9. A complex as recited in claim 6 wherein the ratio of the relative ECL capability of the complex to the relative ECL capability of its bipyridyl analog is greater than or equal to 0.25.

* * * * *